(12) United States Patent
Takakura et al.

(10) Patent No.: US 6,660,851 B1
(45) Date of Patent: Dec. 9, 2003

(54) DNA FRAGMENT ELEVATING GENE EXPRESSION DOSE

(75) Inventors: Yoshimitsu Takakura, Shizuoka (JP); Jun Ueki, Shizuoka (JP)

(73) Assignee: Japan Tobacco Inc., Tokyo (JP)

(*) Notice: Subject to any disclaimer, the term of this patent is extended or adjusted under 35 U.S.C. 154(b) by 14 days.

(21) Appl. No.: 09/807,897

(22) PCT Filed: Aug. 18, 2000

(86) PCT No.: PCT/JP00/05539

§ 371 (c)(1),
(2), (4) Date: Apr. 19, 2001

(87) PCT Pub. No.: WO01/14543

PCT Pub. Date: Mar. 1, 2001

(30) Foreign Application Priority Data

Aug. 19, 1999 (JP) .............................. 11-232815

(51) Int. Cl.[7] .......................... C07H 21/04; C12P 21/00
(52) U.S. Cl. ................. 536/24.1; 435/69.1; 435/320.1; 435/468
(58) Field of Search ...................... 536/24.1; 435/69.1, 435/320.1, 468

(56) References Cited

U.S. PATENT DOCUMENTS 6,235,888 B1 * 5/2001 Pachuk et al. ........... 536/23.72

FOREIGN PATENT DOCUMENTS

| JP | A3103182 | 4/1991 |
| WO | A19943818 | 9/1999 |

OTHER PUBLICATIONS

Mascarenhas et al., Plant Molecular Biology, vol. 15, pp. 913–920 (1990).

* cited by examiner

Primary Examiner—David Guzo
Assistant Examiner—David A. Lambertson
(74) Attorney, Agent, or Firm—Birch, Stewart, Kolasch & Birch, LLP

(57) ABSTRACT

A novel DNA fragment capable of enhancing the expression level of a gene. The DNA fragment according to the present invention contains a nucleotide sequence from one of the nucleotides at around positions 1- to 152 to one of the nucleotides at around positions 259 to 374 in the sequence represented by SEQ ID NO:1 and is capable of enhancing the expression level of a gene.

15 Claims, 4 Drawing Sheets

Construction of various vectors for analyzing promoter expression

Analysis of 213 promoter expression in various organs
L  R  P  A  Lo P&L BS

Preparation of ATG-free fragment by linking PCR

Structure of 5'-leader of RPC213 gene and construction of plasmids for analyzing expression

DNA FRAGMENT ELEVATING GENE EXPRESSION DOSE

RELATED APPLICATION

This application is the national phase under 35 U.S.C. §371 of PCT International Application No. PCT/JP00/05539 which has an International filing date of Aug. 18, 2000, which designated the United States of America and was published in Japanese.

The present application claims priority from Japanese Patent Application Hei 11-232815 the disclosure of which is incorporated herein by reference.

1. Technical Field to Which the Invention Belongs

This invention relates to a novel DNA fragment which has the effect of remarkably enhancing the expression of a gene.

2. Prior Art

In recent years, molecular breeding using genetic engineering techniques has been intensively applied. However, a problem exists in using such techniques that in a case where a foreign gene is to be expressed in a plant the gene transferred into the plant is not always expressed at a sufficiently high level, and an expression is, in fact, lower than expected. In attempting to produce a substance in a plant, it is requisite to express a transferred gene at a high level. Accordingly, the development of techniques capable of achieving high gene expression is of prime importance.

One technique used for promoting the expression of foreign genes is the use of DNA fragments having a nucleotide sequence capable of promoting gene expression. Examples of these DNA fragments include 5'-untranslated leader sequences and intron sequences. For example, it has been reported that the expression of a foreign gene can be promoted by inserting the first exon (5'-untranslated leader sequence) of corn Shrunken-1 gene (Maas et al., Plant Mol. Biol. 16:199–207, 1991) or the first intron of castor bean catalase gene (JP (Kokai) HEI 3-103182) into the upstream of the foreign gene and then expressing the foreign gene. It has also been reported that some other 5'-untranslated leader sequences and intron sequences originating in plants promote gene expression (Koziel et al. Plant Mol. Biol. 32:393–405, 1996).

The effect of promoting gene expression of an intron sequence is affected by the length of the adjacent exon sequences. In the case of the sixth intron of corn alcohol dehydrogenase 1 gene, for example, a maximum effect is established when a 76 bp exon is located in the 5'-side adjacent to the intron and a 53 bp exon is located in the 3'-side adjacent thereto (Mascarenhas et al. Plant Mol. Biol. 15:913–920, 1990).

In addition, the amplification of gene expression by an intron is affected by various factors such as the promoter used, the plant species involved, and the nucleotide sequence of a structural gene (Koziel et al. Plant Mol. Biol. 32:393–405, 1996). It is to be noted that not every 5'-untranslated leader sequence or intron sequence promotes gene expression. Accordingly, it is strongly desired to further identify various types of 5'-untranslated leader sequences and intron sequences capable of sufficiently amplifying gene expression.

SUMMARY OF THE INVENTION

An object of the present invention is to provide a novel DNA fragment which is capable of remarkably enhancing gene expression.

Another object of the present invention is to provide a method of remarkably enhancing gene expression, in particular expression of a foreign gene, in a host by using the novel DNA fragment.

BRIEF DESCRIPTION OF THE DRAWINGS

In FIG. 1, B, Bg, H, Sc and S1, respectively, stand for BamHI, BglII, HindIII, SacI and SalI.

DETAILED DESCRIPTION OF THE INVENTION

Figure 1:
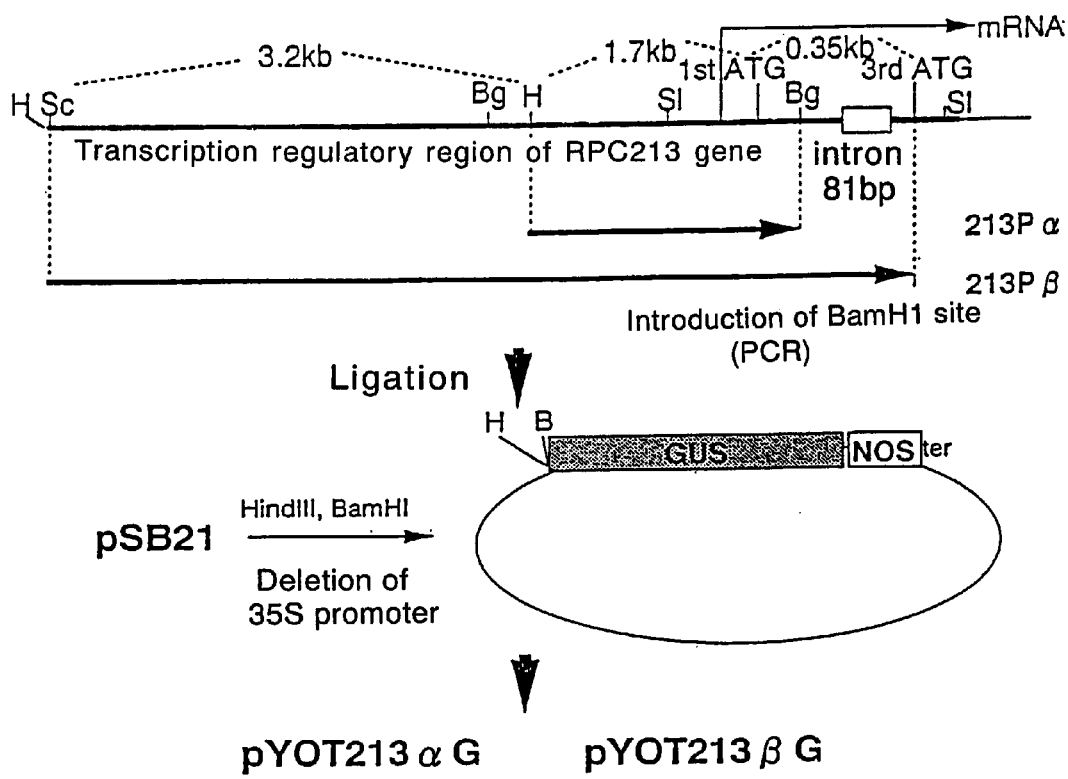
FIG. 1 shows a process of constructing vectors for analyzing the expression of a promoter.

As a result of intensive study, the present inventors have found that a DNA fragment, which comprises the sequence (SEQ ID NO:1) from around the transcription initiation point to immediately before the third ATG of a gene (PRC213 gene; SEQ ID NO:3) which can be isolated as the gene expressed predominantly in rice flower organs, or a part of said DNA fragment, strongly promotes gene expression regardless of whether an intron is contained in the DNA fragment.

Now, the present invention will be described in detail.

The DNA fragment of the present invention was observed to have the effect of enhancing gene expression during the course of analyzing the promoter expression of RPC213 gene. Thus, the DNA fragment was inserted between a cauliflower mosaic virus 35S RNA gene promoter and β-glucuronidase (GUS) gene and introduced into a corn protoplast expression system whereby it has been confirmed that a remarkable potentiation of GUS activity was attained as compared with a system where the novel fragment is not introduced. This effect is not specific to rice flower organs but is reproduced in many plant cells. The RPC213 gene can be isolated as a gene predominantly expressed in rice flower organs from, for example, a paddy rice variety IR24 as will be described in Example 1 hereinafter.

In the first embodiment of the present invention, a genomic sequence provided from the transcription initiation point to immediately before the third ATG of the. RPC213 gene is represented by SEQ ID NO:1 in the Sequence Listing. This sequence contains an 81 bp intron and consists of 374 nucleotides. It has been confirmed that gene expression can be enhanced by 90-fold or more by inserting this sequence between the promoter and the gene to be expressed, using the above-described expression system, as compared with a case where no such insertion is performed. The sequence corresponds to the nucleotide sequence disclosed from position 4996 to 5369 in SEQ ID NO:4, which is the nucleotide sequence of the RPC213 genomic clone (RPG106—see Example 2 E as will be given hereinafter).

In the second embodiment of the present invention, there is provided a modified genomic sequence represented by SEQ ID NO:7. This sequence is almost the same as the genomic sequence represented by SEQ ID NO:1 derived from the RPC213 gene, but the T (thymine) residues of two ATGs located in different reading frames have been converted into A (adenine). After splicing the intron from this sequence, therefore, the resultant sequence contains no ATG. Thus the possibility that the translation of the gene would be initiated from the ATG of RPC213-origin is eliminated. It has been confirmed that this sequence very strongly potentiates gene expression, using the above-described expression system (i.e., about 60-fold).

In the third embodiment of the present invention, there is provided a modified genomic DNA sequence represented by SEQ ID NO:5. This sequence consists of 325 nucleotides formed by deleting 34 bp in the 5'-side and 15 bp in the 3'-side from the sequence represented by SEQ ID NO:1, and by converting T (thymine) in the sole ATG (i.e., the second ATG of RPC213) contained in SEQ ID NO:1 into A (adenine). The 81 bp intron is contained therein. The sequence corresponds to the nucleotide sequence disclosed from position 5030 to 5354 in the sequence represented by SEQ ID NO:4, and it has been confirmed that the sequence strongly potentiates gene expression (i.e., by about 11-fold). After splicing the intron from this sequence, the resultant sequence contained no ATG. Thus the possibility that the translation of the gene would be initiated from the ATG of RPC213-origin is eliminated.

In the fourth embodiment of the present invention, there is provided a sequence represented by SEQ ID NO:2. This sequence consists of 108 nucleotides formed by adding a 15 bp exon sequence to the 5'-side and a 12 bp exon sequence to the 3'-side of the 81 bp intron sequence of the RPC213 gene. The sequence corresponds to the nucleotide sequence disclosed from position 5147 to 5254 in the sequence represented by SEQ ID NO:4, and it has been confirmed that the sequence potentiates gene expression by about 4-fold. After splicing the intron from this sequence, the resultant sequence contains no ATG.

In the fifth embodiment of the present invention, there is provided a cDNA sequence represented by SEQ ID NO:8. This sequence corresponds to the cDNA of the RPC213 gene from the transcription initiation point to immediately before the third ATG. The sequence contains no introns and consists of 293 nucleotides. Furthermore, SEQ ID NO: 8 corresponds to the nucleotide sequence disclosed from position 2 to 294 in the sequence represented by SEQ ID NO:3, but the T (thymine) residues of two ATGs located in different reading frames have been converted into A (adenine). Thus the possibility that the translation of the gene would be initiated from the ATG of RPC213-origin is eliminated. It has been confirmed that the sequence strongly potentiates gene expression (by about 10-fold).

These results indicate that the DNA structure from the transcription initiation point to immediately before the third ATG of the endogenous RPC213 gene in plant cells is optimal for the regulation of gene expression and, in particular, the regulation of transcription. Although potentiation expression was lowered by deleting the intron from said DNA comprised from the transcription initiation point to immediately before the third ATG (the fifth invention), potentiation of expression by about 4-fold was achieved substantially by the intron alone. Based on these facts, it is estimated that the intron and the primary structure of the intron-free DNA from the transcription initiation point to immediately before the third ATG exerts a synergistic effect in potentiating expression.

Accordingly, the present invention provides the DNA fragment comprising the sequence represented by SEQ ID NO:1 or a part thereof, DNA fragments comprising the above-described sequence either containing or not containing the intron, and DNA fragments which can be easily obtained by modifying the above-described DNA fragment and still maintain potentiation of gene expression (for example, a DNA fragment containing a nucleotide from one of the nucleotides at around positions 1 through 151 to one of the nucleotides at around positions 259 through 374, which may or may not contain the intron, and which is capable of enhancing the expression a gene).

The DNA fragment comprising the sequence represented by SEQ ID NO:1 can be isolated from rice as will be described in Examples given hereinafter. Alternatively, it can be easily obtained by PCR, using the rice genome as a template and two oligonucleotides complementary to each end of the sequence respectively, represented by SEQ ID NO:1, as primers. Alternatively, the fragment can be prepared by synthesizing the full sequence or parts thereof by using a DNA synthesizer, followed by appropriate ligation. Also, the sequences comprising the nucleotides represented by SEQ ID NOS:2, 5, 7 or 8 can be prepared as will be described in the following Examples, or it is possible to prepare these sequences by synthesizing the full sequence or parts thereof by using a DNA synthesizer followed by appropriate ligation.

It is well known in general that physiologically active DNA frequently maintains substantially the same activity after its nucleotide sequence has been partly modified. Thus, DNA fragments having sequences derived from the sequences represented by SEQ ID NOS:1, 2, 5, 7 or 8 or a part thereof by deletion, substitution, insertion or addition of one or more nucleotides also fall within the scope of the present invention, so long as they potentiate gene expression. The deletion, substitution, insertion or addition of nucleotide(s) can be performed by, for example, site-directed mutagenesis which is a well known technique (see, for example, Nucl. Acids Res. 10:6487–6500, 1982). The expression "one or more nucleotides" as used herein means a number of nucleotides such as allows deletion, substitution, insertion or addition by the site-directed mutagenesis method. For instance, the deletion, substitution, insertion or addition of 10 or less nucleotides, preferably 5 or less nucleotides. Site-directed mutagenesis can be carried out in the following manner with the use of a synthetic oligonucleotide primer which is complementary to the single-stranded phage DNA to be mutated, excluding a specific disagreement corresponding to the desired mutation. Namely, a complementary chain is synthesized by the phage with the use of the above-described synthetic oligonucleotide as the primer, and then a bacteria host carrying the phage is transformed by the double-stranded DNA thus obtained. The culture of the transformed bacterium is plated on agar, and plaques are formed from individual cells carrying the phage. Thus, theoretically 50% of new colonies have the mutated phage carrying the mutation in the single chain while the remaining 50% of colonies carry the intact sequence. Then the obtained plaques are hybridized with a synthetic probe, having been treated with a kinase, at a temperature at which the plaques having the same sequence as the above-described mutated DNA are hybridizable but those having the intact sequence are not. Next, the plaques hybridizable with the probe are taken up and incubated to thereby collect the DNA.

It is anticipated that DNA fragments which have the same effect of potentiating gene expression as the DNA fragment according to the present invention but which differ somewhat in sequence from the sequence represented by SEQ ID NO:1 may be obtained by PCR with the use of a plant genome other than rice as a template, and two oligonucleotides respectively complementary to both ends of the sequence represented by SEQ ID NO:1 as primers. Generally speaking, such DNA fragments are hybridizable under stringent conditions with a DNA fragment comprising the sequence represented by SEQ ID NO:1. Accordingly, such DNA fragments are also included in the scope of the present invention, so long as they are capable of enhancing the expression of a gene. The term "stringent conditions" as used herein means, for example, from room temperature to 42° C. in the presence of 6×SSC, 5×Denhart's solution, 0.1% SDS and 50% formamide.

The DNA fragment according to the present invention potentiates gene expression. The terms "potentiating" or "enhancing gene expression" as used herein mean that when a DNA fragment according to the present invention is integrated into the upstream, downstream, or preferably between a promoter and a gene controlled by this promoter, expression of the gene is elevated at least 1-fold (preferably 2-fold, still preferably 3-fold or more) compared with a case where no such. integration is made. Although the gene to be potentiated with regard to the expression thereof is preferably a foreign gene, it may be a gene inherent to the cell.

To confirm the potentiation of gene expression of the DNA fragment according to the present invention, any expression system may be used. For example, it is advantageous to use a transient assay as will be described in Example 4 hereinafter.

The present invention further provides a method which comprises integrating one of the DNA fragments of the present invention into a DNA construct comprising a DNA fragment wherein a foreign gene to be expressed in host cells is located downstream of a promoter and then transforming the host cells by the DNA construct, thereby potentiating a higher expression of the foreign gene in the host cells compared with the case where the host cells are transformed by a DNA construct free from the DNA fragment.

Examples of the host cells include eucaryotic cells such as animal cells, plant cells and fungus cells. It is preferred to use plant cells, still preferably monocotyledonous cells.

The foreign gene may be any gene which can be expressed in the host cells employed. It may be a gene either encoding or not encoding a protein, for example, a gene for allowing the transcription of an antisense RNA.

The promoter may be any promoter capable of functioning in the host cells employed. In the case of using plant cells as the host cells, for example, it is preferable to employ cauliflower mosaic virus 35S promoter, ubiquitin promoter, actin promoter, PPDK promoter, PEPC promoter, etc.

The DNA fragment according to the present invention can be integrated by ligating the DNA fragment of the present invention together with a promoter and a foreign gene under control of acid promoter to a vector or a plasmid compatible with the host and then transforming the host cells with this vector or plasmid. It is preferred that the vector or plasmid has a marker for screening the transformant. Although the DNA fragment of the present invention is integrated preferably between the promoter and the foreign gene, the integration site is not limited thereto so long as the DNA fragment can achieve its effect of potentiating gene expression. According to the present invention, the transformed host cells may carry the DNA fragment, the promoter, and the foreign gene in a state where they are either integrated into the chromosome or integrated into the expression vector.

The expression of the foreign gene may be either the transcription rate of the foreign gene, the accumulation of the transcriptional product, the accumulation of a protein or, in the case where the protein is an enzyme, an enzymatic activity.

Now, the present invention will be illustrated in greater detail with reference to the following Examples.

EXAMPLES

Example 1

Isolation of RPC213 cDNA

Paddy rice varieties "Tsukinohikari" and "IR24" were grown in a greenhouse and subjected to the following experiments.

A) Extraction of RNA

The leaf, immature pistil, mature pistil, anther, lodicule, palea and lemma, immature seed, germinating seed, root, callus and immature spikelet (4.5 to 6.0 mm in length) of "IR24" were collected, immediately frozen in liquid nitrogen and then stored at −80° C. The total RNA was extracted from these tissues by the phenol-SDS method (Watanabe and Price, Proc. Natl. Acad. Sci. USA, 79, 6304–6308, 1982) except that β-mercaptoethanol was added as an antioxidant to the extraction buffer to give a final concentration of 10% (V/V). The tissues to be used in the reverse transcription PCR experiment were treated with DNase I (FPLCpure, manufactured by Pharmacia) in the presence of RNase inhibitor (RNAguard, manufactured by Pharmacia), rather than being subjected to lithium chloride precipitation, so as to minimize the contamination with any trace amount of DNA. 0.375 $\mu g/\mu l$ of the total nucleic acid and 1.75 U/$\mu l$ of RNase inhibitor were added in a buffer (40 mM Tris-Cl pH 7.5, 6 mM MgCl$_2$) and 0.375 U/$\mu l$ of DNase I (each expressed in the final concentration) was added thereto. After maintaining at 37° C. for 10 to 30 minutes, DNase I was inactivated by extracting with phenol/chloroform.

The leaf and root [expressed in root(soil) in Table 1 as will be given hereinafter] were collected from a plant grown for 1 month at the greenhouse after sowing. The immature pistil was collected from a plant 1 to 2 weeks before earing. The mature pistil, anther, lodicule and palea and lemma were collected from a plant immediately to several days before flowering. The immature seed was collected from a plant 1 to 2 weeks after flowering. The germinating seed and root were obtained from a plant aseptically grown on an N6 medium (Chu et al. Scientia Sinica, 18, 659–668, 1975) respectively for 1 and 3 weeks after sowing. The callus was induced from a seed in an N6 solid medium containing 2 mg/l of 2,4-D and then cultured before use in a liquid medium of the same composition under shaking for 3 weeks. The total RNA of the pistil and leaf was purified to provide polyA+RNA by using Oligotex-dT30 super (manufactured by Takara Shuzo Co., Ltd.) in accordance with the manufacturer's instructions.

B) Construction of Pistil cDNA Library

About 1 $\mu$g of polyA+RNA isolated and purified from pistil was employed as a template to synthesize the cDNA by using ZAP-cDNA Synthesis Kit (manufactured by STRATAGENE). The cDNA was connected to an EcoRI adapter in accordance with the manufacturer's instructions, digested with XhoI and then ligated into a vector UniZAP XR. Next, the phage DNA was packaged into phage particles by using Giga pack Gold packaging extract (manufactured by STRATAGENE).

C) Differential Screening

Differential screening was carried out in accordance with the method of Takakura et al. (WO98/29542). When about 30,000 plaques were examined, 198 plaques showing intense hybridization signals with the pistil probe but only weak signals with the leaf probe were selected by the primary screening. 152 clones among them were subjected to the secondary screening. To avoid intense background of plaque hybridization in this step and to efficiently perform screening, the following method was employed. First, the plaques selected by the primary screening were stored in 200 μl of SM buffer (0.1 M NaCl, 7 MM MgSO$_4$, 50 mM Tris-Cl pH 7.5, 0.01% gelatin) containing one drop of chloroform at 4° C. Then the thus stored liquid was diluted and the phage was plated so as to give a considerably low plaque density (10 to 100 pfu/plate). A single plaque was isolated and stored in the same buffer. From this liquid, a plating lysate containing the phage at a high concentration was prepared and in vivo excision was performed in accordance with the instructions attached to ZAP cDNA Synthesis Kit. Thus a plasmid [pBluescriptSK(−)] was prepared from the phage genome.

Then the plasmid was digested with restriction enzymes EcoRI and XhoI (manufactured by Takara Shuzo Co., Ltd.) and thus a cDNA insert was isolated and purified. This cDNA insert was fractionated by electrophoresis on a 0.8% agarose gel and transferred onto a nylon membrane filter HybondN+. Then differential hybridization was carried out with the use of pistil and leaf probes, as well as single-stranded cDNA probes synthesized by using Oligo dT Primer from the total RNA of anther, germinating seed, root, callus and immature seed. As a result, 6 cDNA clones which hybridize with the pistil probe but little with other probes were obtained. Among these clones, one having an insert cDNA of about 1.5 kb was named "RPC213" and employed in the subsequent experiments.

D) Analysis of Organ-specific Expression of cDNA Clones

The cDNA clone "RPC213" screened in the above C) was subjected to Northern hybridization to examine the expression patterns and expression levels in various organs. Filters were prepared in the following manner.

First, the secondary structure of the total RNA (20 μg) from each of the organs described in above A) was removed in accordance with the method of Sambrook et al. (Molecular Cloning, 1982) with the use of deionized Glyoxal and DMSO and then fractionated on 1% agarose gel. Next, the RNA was transferred onto a nylon membrane Gene Screen Plus (manufactured by DU PONT) by the conventional method. After drying in vacuo at 80° C. for 1 hour, the filter was boiled in 20 mM Tris-Cl (pH 8.0) for 5 minutes to remove Glyoxal. As the probe, the 1.5 kb EcoRI-XhoI fragment of the above-mentioned cDNA was RI-labeled by using Multiprime Labeling System (manufactured by Amersham). Pre-hybridization and hybridization were carried out in accordance with the manufacturer's instructions attached to the filter. The filter was successively washed with 2×SSC, 1% SDS and 0.2×SSC, 1% SDS at room temperature each for 5 minutes, then twice with 0.16×SSC, 1% SDS at 65° C. for 15 minutes, and then with 2×SSC at room temperature for 1 minute. Subsequently, Kodak X-Omat Film was exposed to the filter at −70° C. overnight.

As a result, an intense hybridization signal was observed in the lane of mature pistil, weak signals were observed in the lanes of palea and lemma and callus, and very weak signals were observed in the lanes of leaf, anther and immature seed, while other lanes showed no signal. Thus, it was clarified by the results of Northern analysis that the isolated clone was relatively strongly expressed in mature pistil and weakly expressed in palea and lemma and callus but scarcely expressed in leaf, anther and immature seed. The size of the transcript was estimated to be about 1.6 kb.

To analyze the organ-specific expression of the cDNA clone at a higher precision, reverse transcription PCR was carried out by using RNA of various rice organs as templates. By using a GENESIS 2000 Fluorescence Sequencer (manufactured by DU PONT), the nucleotide sequence of the cDNA inserted into the plasmid pBluescript SK(−) was first partly determined. In accordance with the manufacturer's instructions attached to the Sequencer, T7 DNA polymerase reaction was performed by using M13. and M4 primers (manufactured by Takara Shuzo Co., Ltd.) followed by electrophoresis on a 6% acrylamide gel. Then, the nucleotide sequence was determined from both of the 5'-(EcoRI) and 3'-(XhoI) sides. Based on the DNA sequence of about 400 nucleotides (mRNA sense strand) in the 3'-side, the following primers:

213S (SEQ ID NO: 9):
5'-CGCTATGGCCCGTTTCAGCT-3' and
213AS (SEQ ID NO: 10):
5'-GTCGTCCTGTCGCTTCATTAC-3' were synthesized with DNA Synthesizer (manufactured by ABI), purified by OPC Cartilage (manufactured by ABI) and employed in the reverse transcription PCR experiment. It is expected that a product of about 250 bp might be amplified with these primers. Also, the following primers synthesized on the basis of the sequence of rice actin 1 gene (RAc1, McElroy et al. Plant Mol. Biol. 14, 163–171, 1990):

(SEQ ID NO: 11)
5'-GTATCCATGAGACTACATACAACT-3' and
(SEQ ID NO: 12)
5'-TACTCAGCCTTGGCAATCCACA-3' were employed in a control. These primers were designed so that an intron was sandwiched between them. In the case where a template DNA was contaminated with genomic DNA, it was therefore expected that a 350 bp product originating in the genomic DNA would be amplified in addition to the cDNA-origin product of 267 bp.

10 μg of the total RNA of each of the above-mentioned organs was mixed with 500 ng of Oligo dT15 Primer (manufactured by Amersham) and the secondary structure thereof was dissociated by treating in 55 μl of the reaction mixture at 70° C. for 10 minutes. After quenching on ice, the mixture was maintained at 37° C. for 60 minutes in 100 μl of a reaction mixture comprising 1×1st strand buffer (manufactured by BRL), 0.5 mM of dNTPmix, 10 mM of DTT, 2 U/μl of RNase inhibitor (RNAguard, manufactured by Pharmacia) and 10 U/μl of reverse transcriptase Superscript (manufactured by BRL) (each expressed in the final concentration). Next, it was treated at 95° C. for 5 minutes to dissociate the RNA-cDNA hybrid and then cooled on ice. The cDNA concentration of this solution was referred to as 100 ng/μl. Next, the synthesized cDNA of each organ was diluted into 4 series concentrations (100 ng/μl, 10 ng/μl, 1 ng/μl, 0.1 ng/μl) and employed as a template in PCR.

PCR was carried out under the following conditions. 1 μl of the cDNA dilution was mixed with 0.5 pmole/μl of primer, 0.2 mM dNTP, 1×PCR buffer and 0.05 U Taq Polymerase (manufactured by Takara Shuzo) (each expressed in the final concentration) to give 20 μl of a reaction mixture. By using GeneAmp 9600 (manufactured by Perkin Elmer), the reaction mixture was subjected to PCR consisting of 3 minutes at 94° C. for 1 cycle, 0.5 minutes at 94° C., 1 minute at 60° C. and 1 minute at 72° C. for 30 cycles and 6 minutes at 72° C. for 1 cycle. The PCR product was electrophoresed on an agarose gel, stained with ethidium bromide and then photographed. Bands were compared with each other in density and 2 samples showing the same density were evaluated as containing cDNA originating from RPC213 gene in the same amount.

As a control experiment, PCR was carried out for the reverse transcription product of the total RNA prepared from each of the organs by using the Racl gene primers seemingly expressed constitutionally in all of rice organs. As a result, the expected 267 bp PCR product was detected from all of the organs examined while the 350 bp product was not detected. Therefore it was considered that the template cDNA was not contaminated with genomic DNA.

By using plasmid clones, it was preliminarily confirmed that a product of the anticipated molecular weight could be amplified with the primers of the RPC213 gene. When reverse transcription PCR was performed by using these primers and 100 ng of cDNA as a template, dense bands of the PCR products were observed in mature pistil, palea and lemma and callus, faint bands were observed in anther and immature seed and very faint bands were observed in leaf, germinating seed and root. Among these organs, mature pistil and palea and lemma showed the PCR product after diluting the template cDNA to 1 ng, while callus, anther and immature seed showed the product only up to the template cDNA dilution of 10 ng. Leaf, germinating seed and root showed no PCR product, when the template cDNA was diluted to less than 100 ng. It was estimated based on the presence or absence or the densities of the band that the expression level in palea and lemma was about 1 to 1/10, those in anther, immature seed and callus were about 1/10 and those in other organs were about 1/100, taking the expression level in mature pistil as 1.

Next, the expression was analyzed with regard to flower organ site and development stage. cDNAs prepared from whole mature pistil, stigma of mature pistil, ovary of mature pistil, whole immature pistil and lodicule were employed as templates. Also, use was made of leaf cDNA and plasmid DNA as controls. First, PCR as a control experiment was carried out by using the actin primers. As a result, the 267 bp product was amplified from all of the template cDNAs. Then PCR was carried out with the use of RPC213-specific primers. As a result, when 10 ng of cDNA was employed as a template, the PCR product was detected in all of the organs but leaf. Among these organs, immature pistil, stigma and lodicule showed the PCR product even though the template was diluted to 0.1 ng, while mature pistil and its ovary showed the PCR product only up to the template dilution of 1 ng. When the RPC213 expression level in the whole mature pistil was taken as 1, it was estimated based on the above results that the expression levels in immature pistil, stigma and lodicule were about 10 and that in ovary was about 1. Namely, the results of the reverse transcription PCR indicate that the RPC213 gene is strongly and predominantly expressed in immature pistil, mature pistil stigma and lodicule but weakly in mature pistil ovary and palea and lemma and scarcely in other organs.

Table 1 summarizes the results of the Northern analysis and the results of the RT-PCR.

TABLE 1

Analysis on RPC 213 gene expression

| Organ/ Analysis method | Mature pistil | Stigma | Ovary | Immature Pistil | Lodicule | Palea/ Lemma | Anther |
|---|---|---|---|---|---|---|---|
| Northern analysis | ++ | NT | NT | NT | NT | + | − |
| RT-PCT | 1 | 10 | 1 | 10 | 10 | 1–0.1 | 0.1 |

| Organ/ Analysis method | Immature seed | Germinating seed | Leaf | Root | Root (soil) | Callus |
|---|---|---|---|---|---|---|
| Northern analysis | ± | − | ± | − | − | + |
| RT-PCT | 0.1 | 0.01 | 0.01 | 0.01 | NT | 0.1 |

++: strong expression; +: weak expression; ±: little expression; −: no expression.
NT: not analyzed.
RT-PCR: expressed in relative value determined by taking the expression level in mature pistil as 1.

E) Determination of the Nucleotide Sequence of RPC213

The entire nucleotide sequence of the-cDNA clone RPC213 (about 1.5 kb), which is expressed specifically in flower organs, was determined in the following manner with the use of Fluorescence Sequencer (Model 373A, manufactured by Applied Biosystems). Based on the nucleotide sequence data obtained by using the M13 primers (manufactured by Takara Shuzo Co., Ltd.) described above, primers were synthesized and the nucleotide sequence in the undecoded region was determined. By repeating this primer walking procedure, the nucleotide sequence of RPC213 having 1496 bp in total was determined. The reading frame with the largest ORF was identified by the ORF analysis. In this reading frame, polyA signal-like sequences (Heidecker and Messing, Annu. Rev. Plant Physiol. 37, 439–466, 1986) were located about 70 bp and 90 bp downstream of the terminator codon TGA. The entire nucleotide sequence of RPC213 is presented in SEQ ID NO:3. The nucleotide sequence of SEQ ID NO:3 has 1524 bp including 28 bp following the transcription initiation points which were added by reference to the nucleotide sequence of genome clone as will be described hereinafter.

Example 2

Isolation of RPC213 Promoter

A) Construction of Genomic Library

Genomic DNA was isolated by the SDS-phenol method and purified by the lithium chloride precipitation method from "IR24" rice leaves about 2 months after sowing. The DNA was first partly digested with a restriction enzyme MboI (manufactured by Takara Shuzo Co., Ltd.) and then subjected to centrifugation on a sucrose density gradient. Sucrose was dissolved in a buffer (20 mM Tris-HCl pH 8.0, 1 mM EDTA, 200 mM NaCl) to give a gradient of 5 concentrations (10, 17.5, 25, 32.5 and 40%). These sucrose solutions were layered in this order from the bottom in a centrifugation tube (40PA, manufactured by Hitachi) and finally the partly digested DNA solution was layered on top of the gradient. After centrifuging at 20,000 rpm for 17 hours at 20° C. by using a rotor SRP28 SA (manufactured by Hitachi), the mixture was fractioned into 80 portions (0.5 ml each) with a peristaltic pump to provide a fraction containing DNA fragments of 16 to 23 kb in the largest amount. This DNA fraction was then ligated into a vector λDASH II/BamH (manufactured by STRATAGENE) with the use of T4 DNA ligase (manufactured by BOEHRINGER MANNHEIM) and then packaged into phage particles by using a Gigapack II Gold packaging extract (manufactured by STRATAGENE).

B) Screening of Clones

About 10,000 pfu of the phage was mixed with *E. coli* SRBP2 for infection and spread across a square Petri dish (14×10 cm). After incubation at 39° C. overnight, a nylon membrane filter Hybond N+ (manufactured by Amersham) was brought into contact with the plaque surface and then processed in accordance with the manufacturer's instructions attached to the filter. The probe used in the plaque hybridization was a 0.6 kb EcoRI-SalI fragment in the 5'-side of the rice flower organ-specific cDNA (RPC213) which was used after being RI-labeled with the use of Multiprime Labeling System (manufactured by Amersham). The hybridization and washing were effected under the same conditions as those specified. in the above Example 1 C). From 100,000 plaques, six positive clones were thus selected. Next, phage DNAs were prepared from these plaques. They served as templates in the PCR which was performed with the use of the RPC213-specific primers 213S and 213AS. As a result, the expected product of about 250 bp was found to have been amplified in two clones named RPG106 and RPG107.

C) Subcloning of Promoter-containing Region

DNA was extracted from the above-mentioned two RPC213 genomic clones, digested with SacI and HindIII (manufactured by Takara Shuzo Co., Ltd.) and then fractionated on a 0.8% agarose gel. Also, DNA was isolated and purified by the phenol-SDS method (Komari et al. Theor. Appl. Genet. 77, 547–552, 1989) from paddy rice plants of varieties "Akihikari" and "IR24" about 1 month after sawing. About 5 μg of DNA was digested with SacI and HindIII and electrophoresed similarly to the above case. Next, the DNA bands were blotted onto a nylon membrane filter HybondN+ (manufactured by Amersham) and Southern hybridization was performed by using as a probe the above-mentioned cDNA fragment of 0.6 kb having been RI-labeled as in Example 1D).

Hybridization and washing were carried out in accordance with the manufacturer's instructions attached to the filter. As a result, a band of the same size as in the case of the total genomic DNA appeared in RPG106. Thus, the SacI fragment (6.0 kb) of RPG106 reacting with the probe was subcloned into the same site of pBluescript. Next, physical maps were formed by using the 4 restriction enzymes (BglII, HindIII, SacI and SalI) to further specify the region containing the promoter.

D) Determination of Entire Nucleotide Sequence of RPG106 SacI-SalI Fragment (5.4 kb)

The genomic clone RPG106 has four BglII sites. By using these restriction sites, subcloning was carried out. Then the nucleotide sequences of both strands were determined by using M13 primer (manufactured by Takara Shuzo Co., Ltd.) with Fluorescence Sequencer (Model 373A, manufactured by Applied Biosystems). The nucleotide sequences in regions which could not be decoded by this method and in the vicinities of restriction sites used in the subcloning were determined by the primer walking method and thus the entire nucleotide sequence of RPG106 SacI-SalI 5.4 kb (total nucleotide sequences of 5396 bp) was determined. This nucleotide sequence is represented in SEQ ID NO:4. A comparison of this nucleotide sequence with the nucleotide sequence of the RPC213 cDNA clone indicated that the cDNA clone isolated by the differential screening was a partial length cDNA but contained the almost complete ORF. Namely, ATG was present 7 nucleotides upstream of the 5'-end of the isolated cDNA clone. The reading frame containing this ATG agreed with the cDNA reading frame as described above. It was also clarified that an 81 bp intron was located between the first ATG and the third ATG present in the same reading frame of the RPC213 gene. Further, the second ATG was located not in frame between the first ATG and the intron. The nucleotide sequence (about 300 bp) in the region from the 5'-end to the first SalI site in cDNA completely agreed with the nucleotide sequence of the genomic DNA RPG106 corresponding to this region except that the intron is not contained.

E) Determination of Transcription Initiation Point

Next, the transcription initiation point was determined by the primer extension method. The following two primers were synthesized:

213Z (SEQ ID NO: 13): 5'-TGCTGGTATGGATGTGATG-3'; and 213Z-2 (SEQ ID NO: 14): 5'-CTGACGAGGCTGTTGCTG-3'.

These primers (10 pmole each) were RI-labeled with [γ-$^{32}$P] ATP at the 5'-end with the use of MEGARABEL Kit (manufactured by Takara Shuzo CO., Ltd.) according to the manufacturer's instructions. 0.1 pmol (0.3×10$^6$ cpm) of these labeled primers and 50 μg of the total RNA of immature spikelet (1 to 2 weeks before earing) or leaf were annealed in the presence of 3 U/μl of an RNase inhibitor (RNAguard, manufactured by Pharmacia) in a buffer (0.25 M KCl, 2 mM Tris-HCl pH 8.0, 0.2 mM EDTA) in a reaction system of 10 μl at 42° C. for 2 hours. After adding 30 μl of another buffer (66 mM Tris-HCl pH 8.3, 6.6 mM MgCl$_2$, 1.3 mM DTT, 0.66 mM dNTP, 130 μg/ml actinomycin D) and 1 μl (200 units) of a reverse transcriptase (SUPERSCRIPT, manufactured by BRL), the mixture was maintained at 42° C. for 1 hour. Then ethanol and ammonium acetate were added to allow precipitation to occur. After washing the precipitate with 70% ethanol, the product was air-dried and then dissolved in an electrophoresis buffer which was prepared by mixing the reaction termination solution of T7 Sequencing Kit (manufactured by Pharmacia) with 0.1 M NaOH and 1 mM EDTA (2:1).

Then the whole solution was heated at 95° C. for 3 minutes and then electrophoresed on 6% acrylamide gel. As a marker to be simultaneously electrophoresed, use was made of the product of a sequencing reaction carried out with T7 Sequencing Kit by using the same primers and a plasmid containing RPG106 BglII 2.3 kb as a template. Also, the products of 10 bp and 50 bp ladders (manufactured by BRL), which had been RI-labeled at the end via an exchange reaction with the use of [γ-$^{32}$P]ATP according to the manufacturer's instructions attached to MEGARABEL kit (manufactured by Takara Shuzo CO., Ltd.), were electrophoresed simultaneously as markers. As a result, no extension product was obtained from leaf RNA in which the gene was not expressed, while two bands (in the case of the 213Z primer) and thee bands (in the case of the 213Z-2 primer) of extension products were detected by using the total RNA of immature spikelet as the template. A comparison with the sequence ladders migrated side by side indicated that the products by these primers were detected at the same position. These results indicated that three consecutive transcription initiation nucleotides "CAA" were located in the RPC213 gene and the transcription was initiated from these cytosine or adenine. A TATA box-like sequence (5'-TATAAAT-3') was located 31 bp upstream of the C (cytosine) of the most upstream transcription initiation point. The distance between this TATA box and the transcription initiation point coincided with other plant genes (Joshi, Nucleic Acids Res., 15, 6643–6653, 1987). Further, there was an imaginary initiation codon (the first ATG) 21 bp downstream of the C of the transcription initiation point.

Example 3

Analysis of RPC213 Promoter Expression

A) Construction of Vectors for Analyzing Promoter Expression and Transformation of Rice To analyze the expression of the isolated promoter in vivo, vectors having a GUS reporter gene ligated therein were constructed in the following manner (FIG. 1). The vector used in this example was pSB21 (Komari et al. Plant J., 10, 165–174, 1996). Use was made of a single HindIII site and BamHI site located at both ends of the 35S promoter contained in this vector.

First, RPG106 SacI 6.0 kbp (pBluescript) was co-digested with HindIII and BglII to give a promoter fragment which is the upstream reagion (about 1.8 kb) of the BglII site located at 87 bp downstream of the first ATG in the RPC213 gene. This fragment was ligated to vector pSB21 having been digested with the same enzymes to delete the 35S promoter. The obtained plasmid vector was named pYOT213αG. In this pYOT213αG, the first ATG of RPC gene and the ATG of the GUS gene are located in the same reading frame. When the translation of the RPC213 gene is initiated from the first ATG, therefore, the GUS protein is translated as a fused protein.

On the assumption that the translation of the RPC213 gene might be initiated from the third ATG, another vector was constructed in the following manner to prepare a promoter fragment comprising a broader range. To amplify a part of the promoter region by PCR, a pair of primers:

213P-5H-2 (SEQ ID NO: 15):
  5'-GACGTGATCCACGGCATTGACG-3'; and 213P 2ndATG-Bam (SEQ ID NO: 16):
  5'-CGGGGATCCGTTCTCCTCCACCCACGC-3';

were synthesized. 213P-5H-2 was located upstream of the unique HindIII site, while 213P 2ndATG-Bam had the nucleotide sequence immediately upstream of the third initiation codon ATG of the RPC 213 gene and a BamHI site. The PCR was performed in a reaction system of 100 μl including these primers (100 pmole each), about 1 μg of DNA obtained by preliminarily alkali-denaturing the template RPG106 and Extaq (manufactured by Takara Shuzo Co., Ltd.).

The reaction mixture was subjected to PCR consisting of 3 minutes at 94° C. for 1 cycle, 1 minute at 94° C., 1 minute at 60° C. and 2.5 minutes at 72° C. for 20 cycles and 6 minutes at 72° C. for 1 cycle. The amplification product was cloned into pCRII (manufactured by Invitrogen) and then the nucleotide sequence was confirmed. This plasmid was digested with HindIII and BamHI and the RPC213 promoter fragment of 2.0 kb was isolated therefrom. Next, it was ligated to the vector pSB21 having been treated with the same enzymes to delete the 35S promoter. The plasmid thus obtained was further digested with HindIII and dephosphorylated, to which was inserted an RPG106 HindIII fragment of 3.3 kb prepared by digesting RPG106 SacI 6. Okb (pBluescript) with HindIII. The resultant plasmid vector was named pYOT213βG. This vector had the GUS gene located downstream to the promoter which comprised a fragment of about 5.3 kb immediately upstream of the third ATG of the RPC213 gene. These vectors thus constructed were each transferred into *Agrobacterium tumefaciens* LBA4404 by tri-parental mating and used in an experiment of the transformation of rice.

Rice transformation was carried out using calli developed from immature rice embryo of the variety "Tsukinohikari" in accordance with the method of Hiei et al. (Plant J., 6, 271–282, 1994).

B) Analysis on Promoter Expression Site by Way of Histological Observation of GUS According to the method of Jefferson et al. (EMBO J., 6, 3901–3907, 1987), various tissues (leaf, root, spikelet in earing and spikelet in flowering) of the rice transformants having pYOT213αG or pYOT213βG introduced thereinto, were stained with GUS with the use of X-gluc (5-bromo-4-chloro-3-indolyl-β-D-glucoric acid) as the substrate in order to histologically observe the tissues under a stereoscopic microscope and an optical microscope. As the organs in spikelet, observation was made of pistil, anther, lodicule, palea and lemma and spikelet base. The GUS expression strength by the promoter was evaluated in 4 grades (FIG. 2).

As a result, many individuals having pYOT213αG introduced therein to were not GUS stained in any organ examined. However, five individuals showed the expression of the GUS gene by the promoter activity in some organs. Among these individuals, pYOT213αG-17 showed GUS expression in pistil and lodicule and very weak expression in palea and lemma and spikelet base. These results almost agreed with the results of Northern hybridization and RT-PCR. The GUS expression by pYOT213αG-4 was seen specifically in pistil. The expression in pistil was observed around the border of stigma and ovary. None of these five individuals showed the GUS expression in leaf, root and anther. Namely, two individuals showed the expression in pistil, while one showed in lodicule. In addition, very weak expression was observed in palea and lemma in four individuals and in spikelet base in three individuals.

On the other hand, the 13 individuals having pYOT213PG introduced thereinto were examined. Among them, five individuals (pYOT213βG-3, 7, 8, 16 and 17) showed no or very weak GUS expression in leaf and root but showed the GUS expression in flower organs, namely, exhibiting the flower organ-specific promoter activity. Among them, two individuals (pYOT213βG-7 and 8) presented results well agreeing to the results of Northern hybridization and RT-PCR, i.e., relatively strong GUS expression in pistil and lodicule and very weak expression in anther. In eight transformants other than those showing the flower organ-specific expression, while the GUS expression in leaf and root was also observed, relatively strong promoter activity in flower organs was observed. For example, pYOT213βG-6, which showed the GUS expression in leaf and root, exhibited much stronger expression in inter alia pistil. Also, weak expression was observed in palea and lemma, anther, lodicule and spikelet base. pYOT213βG-17 showed very weak or no expression in leaf and root but relatively strong expression in pistil. In pistil of the transformants having pYOT213βG introduced thereinto, the GUS expression was observed mainly in stigma, i.e., stigma axis and hairy tissues in stigma.

Figure 2:
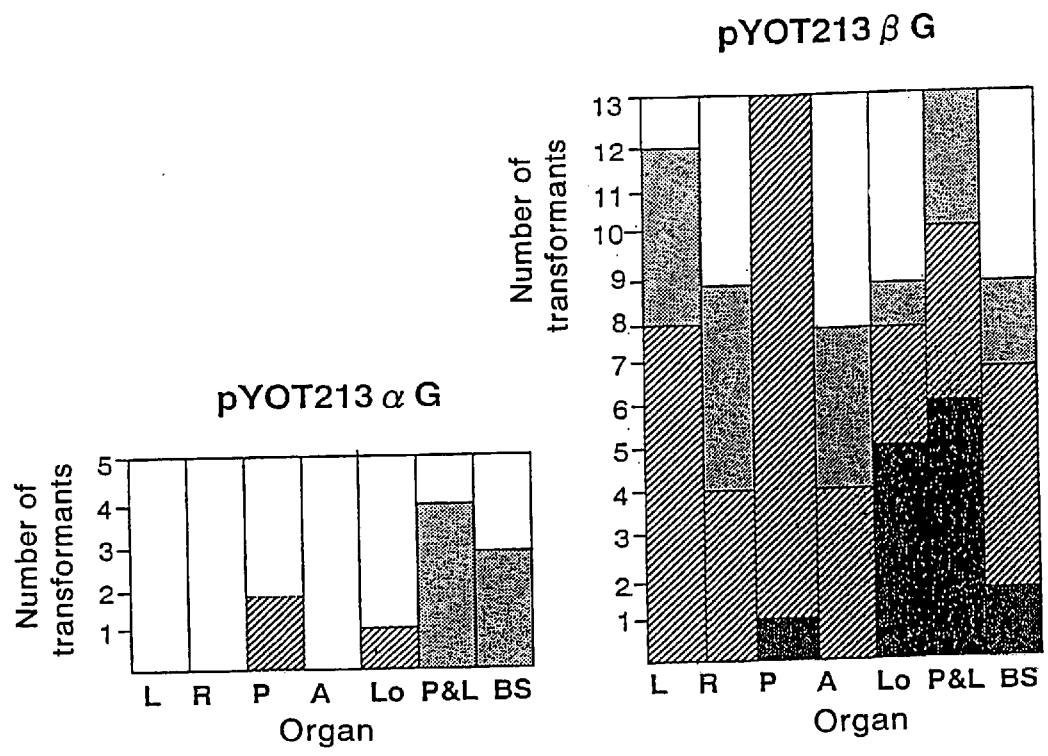
FIG. 2 consists of graphs wherein a summary of the results is shown of the analysis of the expression sites of the 213 promoter by using GUS. In each graph, the abscissa indicates the organs of transformants wherein the GUS expression is examined, while the ordinate indicates the number of transformants showing the expression in the corresponding organ. In each graph, a black bar represents strong expression, a striped bar moderate to weak expression, a gray bar very weak expression, and a white bar no expression. In addition, L denotes leaf, R is for root, P is for pistil, A for anther, Lo lodicule; P&L palea/lemma; and BS spikelet base.

The results of the examination of the GUS expression in the organs as summarized in FIG. 2 indicated that no individual showed strong expression in leaf and root. Slightly more than ½ of the individuals showed moderate to weak expression in leaf, while ⅓ or less of the individuals showed moderate to weak expression in root. The remaining individuals showed very weak or no expression in these tissues. In flower organs, in contrast, strong promoter activity was observed in all organs except anther (i.e., pistil, lodicule, palea and lemma and spikelet base). In particular, all of the 13 individuals showed clear GUS expression in pistil and one of them showed an intense blue-stained GUS image, thus indicating strong expression. In lodicule and palea and lemma, the expression of the GUS gene by the promoter activity was observed in about ⅔ of all the individuals and more than ½ thereof (five and six individuals, respectively) showed strong GUS expression. Also, two individuals showed strong expression in spikelet base.

Based on these results, it has been clarified that these two DNA fragments linked to the GUS gene have promoter activities predominant in flower organs. It is also found that 213β having a longer fragment has the stronger activity. Since the promoter activity of 213β is higher than that of 213α, but these promoter fragments are similar to each other in organ-specificity, it is estimated that a nucleotide sequence regulating the expression level of the RPC213 promoter (contributing to enhanced expression thereof) will be contained either in the SacI-HindIII 3.3 kb fragment, which is contained in the nucleotide sequence of 213β in the region 5' to 213α but not in the nucleotide sequence of 213α, or in the DNA sequence from BglII to the third ATG in the region 3' to 213α.

Example 4

Figure 3:
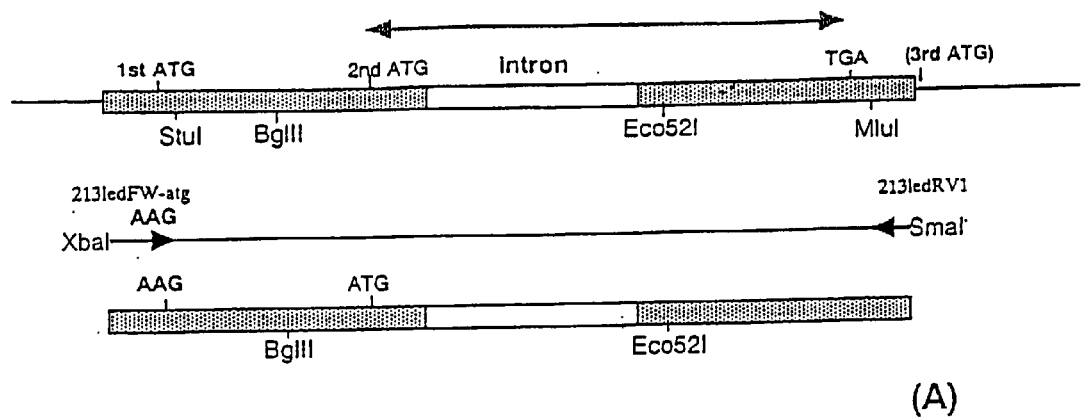
FIG. 3 shows a process of preparing an ATG-free fragment.
Figure 3:
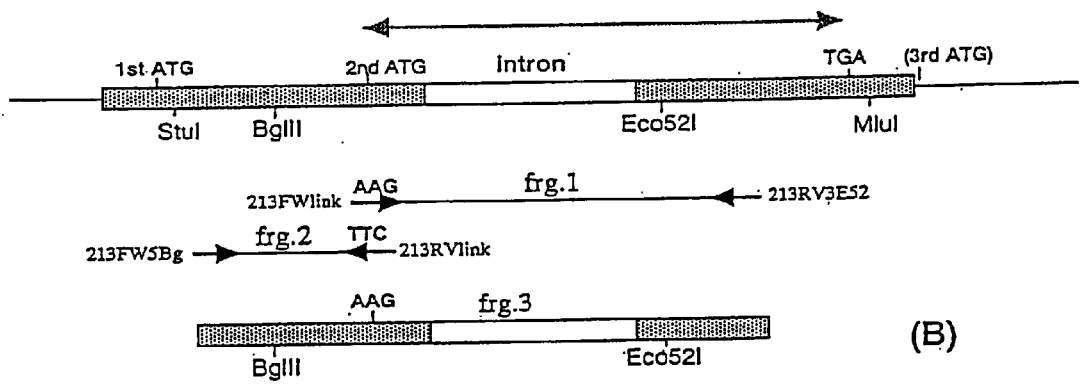
Figure 3:
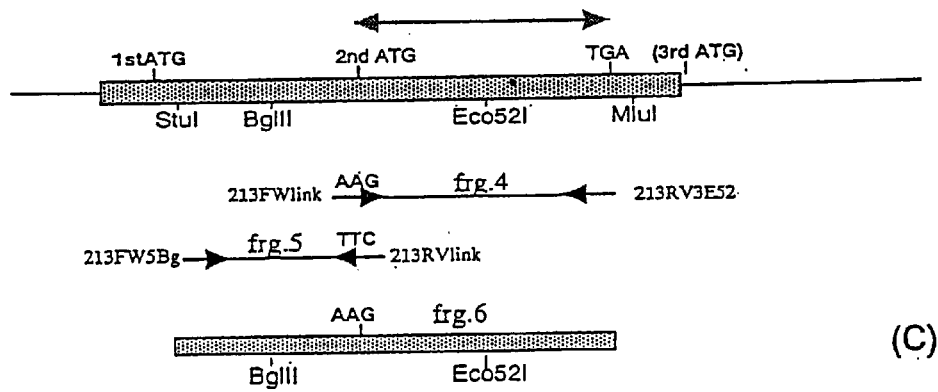
Figure 4:
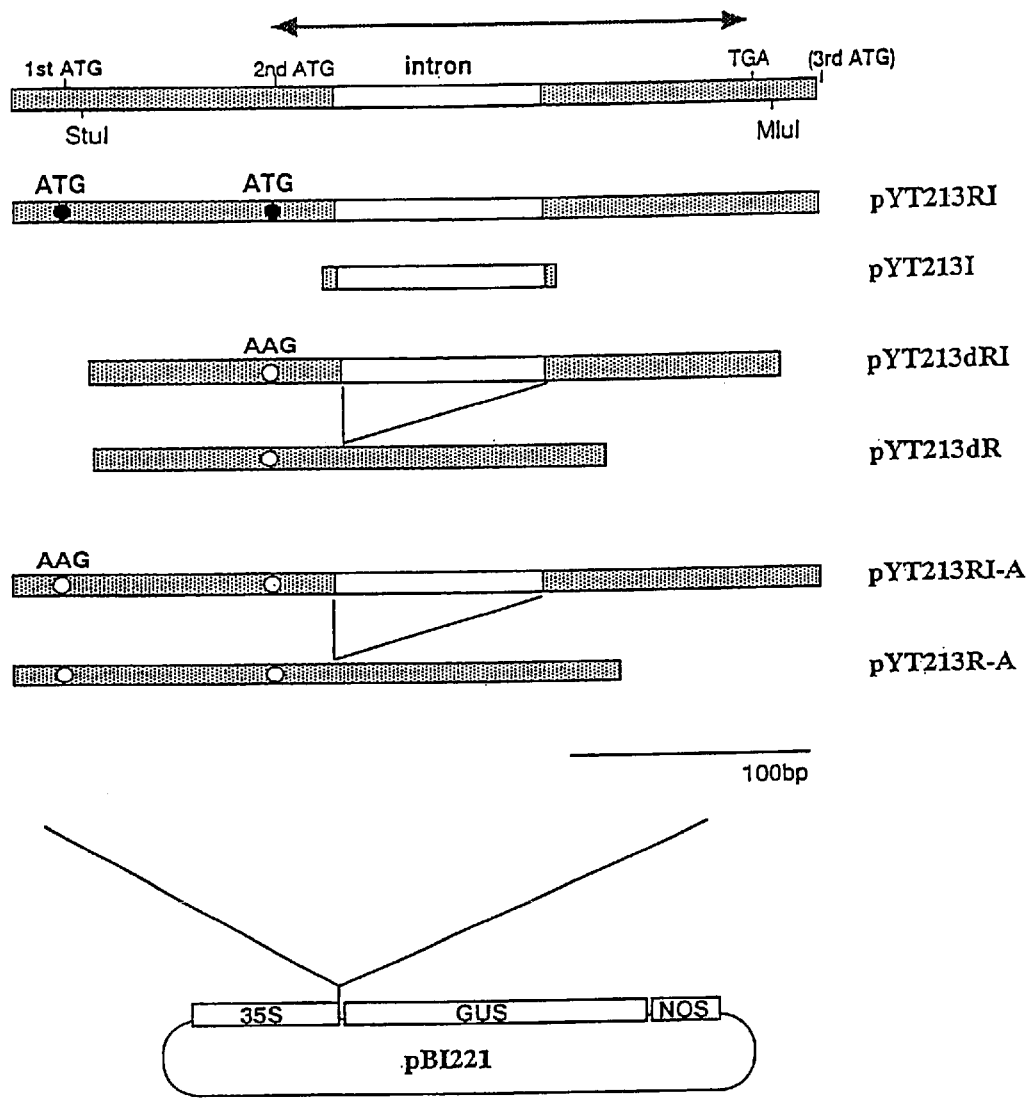
FIG. 4 shows the structures of the plasmids used in the transient assay.

Analysis of Gene Expression Potentiating Effects of the First Intron Sequence of RPC213 Gene, Exon Sequence from the Transcription Initiation Point Adjacent to the First Intron to the Third ATG, and Sequence Consisting of Both of these Sequences The RPC213 gene has the first ATG 21 bp downstream to the most upstream transcription initiation point. An 81 bp intron (first intron) is located 146 bp downstream to the first ATG while the third ATG is located 354 bp downstream to the first ATG. When the splicing of the intron arises, these two ATGs are placed in the same reading frame. Although another ATG (second ATG) is present 112 bp downstream to the first ATG in a different reading frame, a termination codon (TGA) in said reading frame appears 23 bp upstream to the third ATG when the splicing of the intron arises, and as a result, a long ORF cannot be constructed (FIGS. 3 and 4). Accordingly, it is considered that the second ATG is not employed as the translation initiation codon of the RPC213 gene in plant cells.

The results of the above-described promoter expression analysis indicate that the region from the first ATG to the third ATG of the 213 gene plays an important role in the regulation of the expression of this gene. Thus, the effect of potentiating gene expression of this region was analyzed.

A) Construction of Plasmids

Based on the DNA sequence data as described above, the first intron of the RPC213 gene and the exon sequence containing the same from the transcription initiation point to immediately before the third ATG were cloned.

A pair of primers as shown below were synthesized for amplifying the first intron:

213inFW1 (SEQ ID NO: 17):
5'-GGGTCTAGACCTGCACGTACTAGGTATAG TAGC-3'; and

213inRV1 (SEQ ID NO: 18):
5'-CACCCCGGGCCGTCGTCCCCTGCAAGG-3'.

Moreover, a pair of primers as shown below were synthesized for amplifying the sequence containing the first intron from the transcription initiation point to immediately before the third ATG:

213ledFW1 (SEQ ID NO: 19):
5'-TCGTCTAGAAAGGCAGAAAAGAAAGCCAA TG-3'; and

213ledRV1 (SEQ ID NO: 20):
5'-AGCGGGCCCGGGTTCTCCTCCACCCACGC-3'.

These primers each had an XbaI or SmaI restriction site integrated for the subsequent cloning. To the DNA fragment which was amplified with the primers for amplifying the intron, a 15 bp exon and a 12 bp exon were added respectively to the 5'-side and the 3'-side, in addition to the 81 bp intron. The DNA fragment containing the first intron and obtained by using the primers for amplifying the sequence from the transcription initiation point to immediately before the third ATG consisted of 374 bp. The PCR mixture comprised, in 50 μl of the reaction mixture, 10 ng of the template DNA (RPG106 SacI 6.0 kb), 10 pmoles of the primers, 0.2 mM of dNTPs, 1×GC buffer (takara) and 2.5 U of Ex-taq. The PCR consisted of 3 minutes at 96° C. for 1 cycle, 1 minute at 96° C., 1 minute at 55° C. and 1 minute at 72° C. for 30 cycles and finally 6 minutes at 72° C. for 1 cycle. The PCR product was once cloned into a vector pCRII (manufactured by Invitrogen) to thereby confirm the nucleotide sequence. As a result, the nucleotide sequence of each of the PCR products completely agreed with the nucleotide sequence of the corresponding template DNA. These two nucleotide sequences are represented by SEQ ID NOS:2 and 1.

Next, the intron thus cloned into pCRII and the sequence containing the same from the transcription initiation point to immediately before the third ATG were excised by co-digesting with XbaI and SmaI and then integrated into vector pBI221 (purchased form CLONTECH) having been digested with the same enzymes (pYT213I and pYT213RI respectively, see FIG. 4).

Even in case where translation is initiated from the first ATG in pYT213RI, the reading frame agrees with the frame of the GUS gene. In this case, 90 amino acid residues will be added to the N-terminal of the GUS protein. To avoid such a possibility, a similar sequence comprising the region from the transcription initiation point of the RPC213 gene to immediately before the third ATG, but containing neither the first ATG nor the second ATG at 112 bp downstream thereof in a different frame, and the first intron was synthesized by PCR.

Thus, a primer comprising the sequence around the first ATG of the RPC213 gene wherein ATG had been substituted by AAG:

213ledFW-atg (SEQ ID NO: 21):
5'-TCGTCTAGAAAGGCAGAAAAGAAAGCC AAAGGCGTC-3';

was synthesized. This was used in combination with the above-described 213ledRV1 and PCR was carried out by using RPG106 SacI 6.0 kb as a template (FIG. 3A). The composition of the PCR mixture and the reaction conditions were as in the case of pYT213RI and pYT213I. The PCR product was cloned into pCRII and the nucleotide sequence was confirmed. Then it was co-digested with restriction enzymes XbaI and SmaI and the obtained fragment was integrated into vector pBI221 having been digested with the same enzymes (plasmid A).

In the RPC213 gene, a restriction site StuI is present 11 bp downstream to the first ATG and another restriction site MluI is present 20 bp upstream to the third ATG. Further, a restriction site BglII is located between the first ATG and the intron and another restriction site Eco52I is located between the intron and the third ATG, as shown in FIG. 3. The above-described RPG106 SacI 6.0 kb was co-digested with restriction enzymes StuI and MluI and the obtained fragment (about 0.32 kb) was blunted at both ends by treating with klenow (takara). Subsequently, this fragment was ligated to a plasmid prepared by digesting pBI221 with SmaI and CIP-treating to thereby construct a plasmid in which a sequence comprising the first intron and the adjacent exon were integrated in the correct direction between the 35S promoter and the GUS gene (plasmid B).

The DNA fragments of RPC213 gene origin contained in the plasmids A and B had each a single ATG (i.e., the second ATG located 112 bp downstream to the first ATG in a different frame). In the case where translation is initiated from this ATG, the translation is likely to terminate within the short ORF as described above. Thus, this ATG was deleted by the linking PCR in the following manner (FIGS. 3B and 3C).

First, a primer comprising the sequence around the second ATG wherein the ATG had been substituted by AAG:

213Fwlink (SEQ ID NO: 22):
5'-CTTCTCCAAGGCCTGTACGG-3';

and a primer complementary thereto:

213Rvlink (SEQ ID NO: 23):
5'-CCGTACAGGCCTTGGAGAAG-3';

were synthesized. Next, a primer located upstream of the above-described BglI site:

213FW5Bg (SEQ ID NO: 24):
5'-CCAATCATCACATCCATACC-3';

and another primer located downstream of the Eco52I site:

213RV3E52 (SEQ ID NO: 25):
5'-CCGCCGCAGTCCACACC-3';

were synthesized. Then PCR was carried out separately by the combination of 213FWlink and 213RV3E52 or, 213FW5Bg and 213RVlink (first PCR, FIGS. 3B and 3C). In the PCR, 800 ng of the template DNA [RPG106 SacI 6.0 kb (FIG. 3B) or RPC213 cDNA (FIG. 3C)], 100 pmoles of the primers, 0.2 mM of dNTPs, 1×Ex-taq buffer (takara) and 5.0 U of Ex-taq were used in 100 µl of the reaction mixture. The PCR consisted of 3 minutes at 98° C. for 1 cycle, 1 minute at 98° C., 1 minute at 60° C. and 1 minute at 72° C. for 15 cycles and finally 6 minutes at 72° C. for 1 cycle. In the case of using the genomic clone (RPG106 SacI 6.0 kb) as the template, a 153 bp fragment (frg. 1 in FIG. 3B) was amplified by the combination of 213FWlink and 213RV3E52 while a 67 bp fragment (frg. 2, ibid.) was amplified by the combination of 213FW5Bg and 213Rvlink, as expected. In the case of using the cDNA clone (RPC213 cDNA) as the template, a 72 bp fragment (frg. 4 in FIG. 3C) and a 67 bp fragment (frg. 5, ibid.) were respectively amplified as expected. After treating with klenow to delete the terminal adenine, these PCR products were purified on gel. Subsequently, the PCR product obtained by the combination of 213FWlink and 213RV3E52 and the PCR product obtained by the combination of 213FW5Bg and 213RVlink were introduced into a single tube. By using these products as templates, the second PCR was carried out. As external primers, 213FW5Bg and 213RV3E52 were used. In the PCR, 100 to 500 ng of the template DNA, 100 pmoles of the primers, 0.2 mM of dNTPs, 1×Ex-taq buffer (takara) and 5.0 U of Ex-taq were used in 100 µl of reaction mixture. The PCR consisted of 3 minutes at 98° C. for 1 cycle, 1 minute at 98° C., 1 minute at 60° C. and 1 minute at 72° C. for 10 cycles and finally 6 minutes at 72° C. for 1 cycle. In the second PCR, a 201 bp fragment (frg. 3 in FIG. 3B) was amplified in case of using the genomic clone (RPG106b SacI 6.0 kb) as the template while a 120 bp fragment (frg. 6 in FIG. 3C) was amplified in case of using the cDNA clone (RPC213 cDNA) each as expected. The 201 bp fragment derived from the genomic sequence as the linking.PCR product was co-digested with restriction enzymes BglII and Eco52I and then integrated into the plasmid A or the plasmid B having been digested with the same enzymes, thereby providing pYT213RI-A and pYT213dRI respectively (FIG. 4). Similarly, the 120 bp fragment derived from the cDNA sequence was co-digested with BglII and Eco52I and then integrated into the plasmid A and the plasmid B having been digested with the same enzymes to thereby provide pYT213R-A and pYT213dR respectively (FIG. 4). The nucleotide sequences of the RPC213 gene-origin DNAs integrated into pYT213dRI, pYT213dR, pYT213RI-A and pYT213R-A are represented respectively by SEQ ID NOS:5 to 8 in Sequence Listing. The RPC213-origin sequence contained in pYT213RI-A comprises the full sequence from the transcription initiation point to immediately before the third ATG containing the intron and thymine (T) residues in the first ATG and the second ATG have been substituted by A (adenine). In pTY213R-A, no intron is contained. In PYT213dRI, 32 bp in the 5'-side and 20 bp in the 3'-side in the sequence of the RPC213 gene-origin sequence of pYT213RI-A have been deleted (i.e., first ATG not contained). Further, the intron sequence has been deleted in pYT213dR.

B) Transient Assay

Protoplasts were isolated from ethiolated corn leaf. The plant material, the growth conditions and the procedure of isolating the protoplasts were basically determined in accordance with Sheen's report (Sheen, Plant Cell 3, 225–245, 1991). The isolated protoplasts were suspended in an electroporation buffer (4 mM Mes-NaOH containing 0.6 M of mannitol and 20 mM of KCl, pH 5.7). The electroporation was performed by using Gene Pulser (manufactured by Biorad) at 125 µF and 400 V/cm. In a single electroporation procedure, use was made of about $1\times10^5$ protoplasts suspended in 0.8 ml of the electroporation buffer, 30 µg of a plasmid DNA containing the GUS gene, 15 µg of pD0432 containing a luciferase gene (Ow et al. Science 234:856–859, 1986) and 75 µg of salmon sperm DNA. After the completion of the electroporation, the protoplasts were incubated in the dark at 25° C. Then the protoplasts were collected and suspended in 75 µl of 50 mM Tris $H_3PO_4$ (pH 7.5). After adding the same amount of Lysis Reagent Luc (manufactured by Toyo Ink MFG., Tokyo, Japan), the mixture was disrupted by ultrasonication to thereby extract the enzymes. GUS assay (fluorescence assay) was carried out in accordance with Jefferson's method. The luciferase activity was assayed by using PicaGene (Toyo Ink MFG.). The GUS activity was standardized by the co-transformed luciferase activity (Leckie et al. Biotechniques 17:52-3, 56-7, 1994).

Table 2 summarizes the results of the transient assay.

TABLE 2

Gene expression potentiating effects of first intron of RPC213 gene, sequence of from transcription initiation point to immediately before third ATG, and sequence containing first intron of from transcription initiation point to immediately before third ATG

| Plasmid | Constrution | Relative GUS activity |
|---|---|---|
| pBI221 | 35Spro-GUS-NOS | 1 |
| pYT213RI | 35Spro-213leader + intron-GUS-NOS | 92.9 |
| pYT213I | 35Spro-213intron-GUS-NOS | 3.9 |
| pYT213dRI | 35Spro-213Δ5' &3' leader + intron-GUS-NOS | 11.3 |
| pYT213dR | 35Spro-213Δ5' &3' leader-GUS-NOS | 0.3 |
| PYT213RI-A | 35Spro-213leader(-ATG) + intron-GUS-NOS | 60.4 |
| pYT213R-A | 35Spro-213leader(-ATG)-GUS-NOS | 10.5 |

Each GUS activity is expressed in the relative value by referring the activity of pBI221 as to 1.

pYT2113RI showed a GUS activity 90 times or more higher than the pBI221 employed as the control. This fact indicates that the sequence containing the first intron of from the transcription initiation point to immediately before the third ATG of the RPC213 gene very strongly potentiates gene expression. The intron sequence alone showed a GUS activity 3.9 times higher than the control (pYT213I).

It is known that the GUS protein generally sustains its activity when expressed as a fused protein. When translation is initiated from the first ATG in the protoplasts originating in corn leaf, there is a possibility in the case of pYT213RI that an amino acid sequence consisting of 90 residues might be added to the N-end of the GUS protein. It is anticipated that the GUS protein might be thus stabilized thereby resulting in the detection of the high GUS activity. From this viewpoint, another construct (ATG-free construct) wherein the translation was not initiated from the RPC213 gene-origin fragment was also tested. As a result, this ATG-free pYT213RI-A also showed a GUS activity 60 times or more higher than the control. This fact indicates that the sequence per se containing the intron of RPC213 from the transcription initiation point to immediately before the third ATG potentiates gene expression at the transcriptional level. This effect can be characterized as powerful. Also, a GUS activity about 10 times higher than the control was observed in the intron-free sequence from the transcription initiation point to immediately before the third ATG (pYT213R-A).

On the other hand, it is clarified that the gene expression potentiation of the sequence from the transcription initiation point to immediately before the third ATG of the RPC213 gene and the same sequence but containing the first intron is considerably lowered by deleting several ten nucleotides from the 5'- and 3'-DNA sequences thereof. Namely, the activity of pYT213dRI corresponded to about ⅙ of the activity of pYT213RI-A (about 11 times higher than the control) while pYT213dR showed no activity. These results suggest that the primary DNA structure of from the transcription initiation point to immediately before the third ATG for regulating the expression and, in particular, regulating the transcription of the endogenous RPC213 gene in plant cells has been optimized.

Based on the above-described results, it has been clarified that the sequence of from the transcription initiation point to immediately before the third ATG of the RPC213 gene, the first intron and the DNA sequence containing both of them by potentiate gene expression respectively by about 10-fold, 4-fold and 60-fold. Therefore, these elements are expected to make a substantial contribution to the elevated expression of foreign genes used in genetic engineering.

What is claimed is:

1. An isolated DNA fragment comprising a nucleotide sequence from one of the nucleotides at around positions 1 to 152 to one of the nucleotides at around positions 259 to 374 in the sequence represented by SEQ ID NO:1 and being capable of enhancing the expression level of a gene.

2. An isolated DNA fragment comprising a nucleotide sequence from the nucleotide at around position 1 to the nucleotide at around position 374 in the sequence represented by SEQ ID NO:1 and being capable of enhancing the expression level of a gene.

3. An isolated DNA fragment comprising a nucleotide sequence from the nucleotide at around the position 35 to the nucleotide at around position 359 in the sequence represented by SEQ ID NO:1 and being capable of enhancing the expression level of a gene.

4. An isolated DNA fragment comprising a nucleotide sequence from the nucleotide at around position 152 to the nucleotide at around position 259 in the sequence represented by SEQ ID NO:1 and being capable of enhancing the expression level of a gene.

5. A DNA fragment comprising a nucleotide sequence wherein said nucleotide sequence is comprised of one of the nucleotides at around positions 1 to 152 to one of the nucleotides at around position 259 to 374 in the sequence represented by SEQ ID NO:1, and wherein said DNA fragment is derived from said nucleotide sequence by the deletion of a part of the sequence from at around position 167 to at around position 247 in the sequence represented by SEQ ID NO:1 and being capable of enhancing the expression level of a gene.

6. A DNA fragment comprising a nucleotide sequence wherein said nucleotide sequence is comprised of one of the nucleotides at around positions 1 to 152 to one of the nucleotides at around position 259 to 374 in the sequence represented by SEQ ID NO:1, and wherein said DNA fragment is derived from said nucleotide sequence by the modification of one or both of the initiation codon ATG appearing first and the initiation codon ATG appearing secondly with a condon other than an initiation codon and being capable of enhancing the expression level of a gene.

7. A DNA fragment containing a nucleotide sequence represented by SEQ ID NO: 1, 2, 5, 7 or 8 or a nucleotide sequence derived therefrom by deletion, substitution, insertion or addition of 10 or less nucleotides and being capable of enhancing the expression level of a gene.

8. An isolated DNA fragment which hybridizes under stringent conditions with a DNA fragment comprising a nucleotide sequence represented by SEQ ID NO: 1, 2, 5, 7 or 8, and capable of enhancing the expression level of a gene.

9. A DNA fragment containing a nucleotide sequence represented by SEQ ID NO:1, 2, 5, 7 or 8 or a nucleotide sequence derived therefrom by deletion, substitution, insertion or addition of 5 or less nucleotides and being capable of enhancing the expression level of a gene.

10. A method of enhancing the expression of a foreign gene comprising:

a) introducing a DNA fragment comprising a nucleotide sequence from one of the nucleotides at around positions 1 to 152 to one of the nucleotides at around positions 259 to 374 in the sequence represented by SEQ ID NO:1 into a DNA construct having a foreign gene to be expressed in host cells at a location downstream of a promoter; and b) transforming the host cells with said DNA construct to thereby enhance the expression of the foreign gene as compared with a case where the host cells are transformed by the same DNA construct except that it does not contain said DNA fragment.

11. A method of enhancing the expression of a foreign gene in monocots comprising:

a) introducing a DNA fragment which hybridizes under stringent conditions with a nucleotide sequence represented by SEQ ID NO:1, 2, 5, 7 or 8 into a DNA construct wherein said DNA construct has a foreign gene to be expressed in monocot cells at a location downstream of a promoter; and b) transforming the monocot cells with said DNA construct to thereby enhance the expression of the foreign gene as compared with a case where the monocot cells are transformed by the same DNA construct except that it does not contain said DNA fragment.

12. The method of claim 11 wherein said monocot cells are rice or corn.

13. The method of claim 11 or 12, wherein said DNA fragment is modified by the deletion, substitution, insertion or addition of 10 or less nucleotides.

14. The method of claim 11 or 12, wherein said DNA fragment is modified by the deletion, substitution, insertion or addition of 5 or less nucleotides.

15. The method of claim 11 or 12, wherein said DNA fragment is comprises the nucleotide sequence represented by SEQ ID NO:1, 2, 5, 7 or 8.

* * * * *

SEQUENCE LISTING

```
<160> NUMBER OF SEQ ID NOS: 25

<210> SEQ ID NO 1
<211> LENGTH: 374
<212> TYPE: DNA
<213> ORGANISM: Oryza sativa L.
<220> FEATURE:
<221> NAME/KEY: misc_feature
<223> OTHER INFORMATION: Variety: IR24 - Tissue: green leaf
      Library name: lambdaDASHII genomic library derived from green leaf
      genomic DNA Clone Name: RPG106 SacI-SalI 5.4 kb
<221> NAME/KEY: misc_feature
<223> OTHER INFORMATION: Strandedness: double  - Topology: linear
      Molecular Type: genomic DNA Feature: nt1, nt2: transcription
      initiation point of RPC 213 gene determined by primer extension
<221> NAME/KEY: misc_feature
<223> OTHER INFORMATION: nt21 - nt23: the first ATG of RPC213 gene
      nt-133 - nt135: the second ATG of RPC213 gene nt-167 - nt247: the
      first intron of RPC213 gene

<400> SEQUENCE: 1
aaaggcagaa aagaaagcca atggcgtctt caggcctcgc agttgcagca acagcctcgt      60
cagcctggct ctgctgcccc aatcatcaca tccataccag cagcagcaga tctcgcaagc     120
atcttcttct ccatggcctg tacgggtctg cacctgcacg tactaggtat agtagctgca     180
actttattca caatgtgatg tcacgttatt atatatgttt cgtcgtcaat ggcggcgaac     240
cttgcagggg acgacggccg ccggtgtgga ctgcggcggc ggccaccgca gcagcgccgg     300
```

```
cggacacggc ggcgtcggcg cggcgggagc aggtggagat cgcccggtcg ctgaacgcgt      360
gggtggagga gaac                                                        374
```

<210> SEQ ID NO 2
<211> LENGTH: 108
<212> TYPE: DNA
<213> ORGANISM: Oryza sativa L.
<220> FEATURE:
<221> NAME/KEY: misc_feature
<223> OTHER INFORMATION: Variety: IR24 - Tissue: Green Leaf
      Library name: lambdaDASHII genomic library derived from green leaf
      genomic DNA Clone name: RPG106 SacI-SalI 5.4 kb
<221> NAME/KEY: misc_feature
<223> OTHER INFORMATION: Strandedness: double - Topology: linear
      Molecular Type: genomic DNA
      Feature: nt16 - nt96: the first intron of RPC213 gene

<400> SEQUENCE: 2

```
acctgcacgt actaggtata gtagctgcaa ctttattcac aatgtgatgt cacgttatta       60
tatatgtttc gtcgtcaatg gcggcgaacc ttgcagggga cgacggcc                  108
```

<210> SEQ ID NO 3
<211> LENGTH: 1524
<212> TYPE: DNA
<213> ORGANISM: Oryza sativa L.
<220> FEATURE:
<221> NAME/KEY: misc_feature
<223> OTHER INFORMATION: Variety: IR24 - Tissue: pistil
      Library name: lambdaZAPII cDNA library derived from pistil mRNA
      Clone name: RPC213
<221> NAME/KEY: misc_feature
<223> OTHER INFORMATION: Strandedness: double - Topology: linear
      Molecular type: cDNA to mRNA Feature: nt1, nt2, nt3: transcription
      initiation points of RPC213 gene determined by primer extension
<221> NAME/KEY: misc_feature
<223> OTHER INFORMATION: nt22-nt24: the first ATG of RPC213 gene
      nt134-nt136: the second ATG of RPC213 gene
      nt295-nt297: the third ATG of RPC213 gene
      nt1276-nt1278: termination codon of RPC213 gene
<221> NAME/KEY: misc_feature
<223> OTHER INFORMATION: nt1343-nt1348: nt1365-nt1370: poly (A) signals
      nt1507-nt1524: poly (A)

<400> SEQUENCE: 3

```
caaaggcaga aaagaaagcc a atg gcg tct tca ggc ctc gca gtt gca gca        51
                        Met Ala Ser Ser Gly Leu Ala Val Ala Ala
                         1               5                  10 aca gcc tcg tca gcc tgg ctc tgc tgc ccc aat cat cac atc cat acc        99
Thr Ala Ser Ser Ala Trp Leu Cys Cys Pro Asn His His Ile His Thr
             15                  20                  25 agc agc agc aga tct cgc aag cat ctt ctt ctc cat ggc ctg tac ggg       147
Ser Ser Ser Arg Ser Arg Lys His Leu Leu Leu His Gly Leu Tyr Gly
         30                  35                  40 tct gca cct gca cgt act agg gga cga cgg ccg ccg gtg tgg act gcg       195
Ser Ala Pro Ala Arg Thr Arg Gly Arg Arg Pro Pro Val Trp Thr Ala
     45                  50                  55 gcg gcg gcc acc gca gca gcg ccg gcg gac acg gcg gcg tcg gcg cgg       243
Ala Ala Ala Thr Ala Ala Ala Pro Ala Asp Thr Ala Ala Ser Ala Arg
 60                  65                  70 cgg gag cag gtg gag atc gcc cgg tcg ctg aac gcg tgg gtg gag gag       291
Arg Glu Gln Val Glu Ile Ala Arg Ser Leu Asn Ala Trp Val Glu Glu
75                   80                  85                  90 aac atg ctc ccg ctg ctc acc ccc gtc gac tcc gcg tgg cag ccg cac       339
Asn Met Leu Pro Leu Leu Thr Pro Val Asp Ser Ala Trp Gln Pro His
                 95                 100                 105
```

-continued

| | |
|---|---|
| gac ttc ctt ccc tgc tcg gcc gcg ggc ggc ggc gag gcg ctg gcg gcg<br>Asp Phe Leu Pro Cys Ser Ala Gly Gly Gly Glu Ala Leu Ala Ala<br>110               115               120 | 387 |
| ttc acg gag ggc gtg gcc gag ctg cgc gcg ggc gcc gcc ggc gtg ccg<br>Phe Thr Glu Gly Val Ala Glu Leu Arg Ala Gly Ala Ala Gly Val Pro<br>     125               130               135 | 435 |
| gac gag gtg ctg gtc tgc ctc gtg ggg aac atg gtg acg gag gag gcg<br>Asp Glu Val Leu Val Cys Leu Val Gly Asn Met Val Thr Glu Glu Ala<br>140               145               150 | 483 |
| ctc ccg acg tac cag agc atg ggc aac cgc gcc gag ggc ctc gcc gac<br>Leu Pro Thr Tyr Gln Ser Met Gly Asn Arg Ala Glu Gly Leu Ala Asp<br>155               160               165               170 | 531 |
| ggc acc ggc gtg agc ccc ctc ccc tgg gcg cgc tgg ctc cgc ggc tgg<br>Gly Thr Gly Val Ser Pro Leu Pro Trp Ala Arg Trp Leu Arg Gly Trp<br>     175               180               185 | 579 |
| acc gcc gag gag aac cgc cac ggc gac ctc ctc aac cgc tac ctc tac<br>Thr Ala Glu Glu Asn Arg His Gly Asp Leu Leu Asn Arg Tyr Leu Tyr<br>190               195               200 | 627 |
| ctc tcc ggc cgc gtc gac atg cgc cag gtc gag gcc acc gtg cac cgc<br>Leu Ser Gly Arg Val Asp Met Arg Gln Val Glu Ala Thr Val His Arg<br>     205               210               215 | 675 |
| ctc ctc cgc aac ggc atg gag atg ctg gcg ccg gcg agc ccg tac cac<br>Leu Leu Arg Asn Gly Met Glu Met Leu Ala Pro Ala Ser Pro Tyr His<br>220               225               230 | 723 |
| ggc ctg atc tac ggc gcg ttc cag gag cgc gcc acc ttc atc tcc cac<br>Gly Leu Ile Tyr Gly Ala Phe Gln Glu Arg Ala Thr Phe Ile Ser His<br>235               240               245               250 | 771 |
| ggc cac acg gcg agg ctc gcg ggg cag cac ggc gac cgg gcg ctc gcc<br>Gly His Thr Ala Arg Leu Ala Gly Gln His Gly Asp Arg Ala Leu Ala<br>     255               260               265 | 819 |
| aag atc tgc ggc gtg atc gcc gcc gac gag agg cgg cac gag gcg ggc<br>Lys Ile Cys Gly Val Ile Ala Ala Asp Glu Arg Arg His Glu Ala Gly<br>270               275               280 | 867 |
| tac acg atg gcg tcc gcc agg ctg ttc gag ctc gac ccg gac ggc atg<br>Tyr Thr Met Ala Ser Ala Arg Leu Phe Glu Leu Asp Pro Asp Gly Met<br>     285               290               295 | 915 |
| gcg cgc gcg ctg gcg gac gtc atg cgc ggg aag gtg acc atg ccg ggg<br>Ala Arg Ala Leu Ala Asp Val Met Arg Gly Lys Val Thr Met Pro Gly<br>300               305               310 | 963 |
| cag ctc atg tcg gac ggc cgc gac ggc gac ggc gag cac agc ctg ttc<br>Gln Leu Met Ser Asp Gly Arg Asp Gly Asp Gly Glu His Ser Leu Phe<br>315               320               325               330 | 1011 |
| gcc cgg ttc tcc gcc gtg gcg gag cgc gcc ggc gtg tac acg gcg agg<br>Ala Arg Phe Ser Ala Val Ala Glu Arg Ala Gly Val Tyr Thr Ala Arg<br>     335               340               345 | 1059 |
| gac tac ggc gaa ctc gtc gag cac ttc gtg cgg agg tgg cgg gtg gcg<br>Asp Tyr Gly Glu Leu Val Glu His Phe Val Arg Arg Trp Arg Val Ala<br>350               355               360 | 1107 |
| gag ctc gcg gcg ggg ctc tcc ggc gag ggc cga cgc gcg cag gag tac<br>Glu Leu Ala Ala Gly Leu Ser Gly Glu Gly Arg Arg Ala Gln Glu Tyr<br>     365               370               375 | 1155 |
| ctg tgc ggg ttg gcg ccc aag atc cgg agg atg gag gag ctg gcc cac<br>Leu Cys Gly Leu Ala Pro Lys Ile Arg Arg Met Glu Glu Leu Ala His<br>380               385               390 | 1203 |
| cgg agg gcg gcc cgc atc gag ccc gct atg gcc cgt ttc agc tgg atc<br>Arg Arg Ala Ala Arg Ile Glu Pro Ala Met Ala Arg Phe Ser Trp Ile<br>395               400               405               410 | 1251 |
| ttc gat agg ccc gtc atg ctg ggc tgatcaaccc ggggcttcgg ttatggtttt<br>Phe Asp Arg Pro Val Met Leu Gly<br>     415 | 1305 |

```
atgggcccgt ttactgggct ctgcttgctc aaattataat aagctacatc gtgtgctaaa    1365
ataatttatc tttgttatta aggattcgtg tgagaaagct attttgtttt ctgtagcaag    1425
tttaggaatg taatgtaatg taatgaagcg gcaggacgac tgccatttga ttaagaaaag    1485
actcgcgctt gtttgtagtc caaaaaaaaa aaaaaaaa                            1524
```

<210> SEQ ID NO 4
<211> LENGTH: 5396
<212> TYPE: DNA
<213> ORGANISM: Oryza sativa L.
<220> FEATURE:
<221> NAME/KEY: misc_feature
<223> OTHER INFORMATION: Variety: IR24
    Library name: lambdaDASHII genomic library derived from green leaf
    genomic DNA Clone name: RPG106 SacI-SalI 5.4 kb
<221> NAME/KEY: misc_feature
<223> OTHER INFORMATION: Strandedness: double - Topology: linear
    Molecular type: genomic DNA Feature: nt1-nt5369, nt3335-nt5108;
    sequences whose promoter activity was confirmed by GUS
<221> NAME/KEY: misc_feature
<223> OTHER INFORMATION: nt4964-nt4969: TATA box like sequence
    nt4995, 4996, 4997: transcription initiation points of RPC213 gene
    determined by primer extension nt5016-nt5018: the first ATG of
    RPC213 gene
<221> NAME/KEY: misc_feature
<223> OTHER INFORMATION: nt5128-nt5130: the second ATG of RPC213 gene
    nt5370-nt5372: the third ATG of RPC213 gene
    nt5162-nt5242: intron
    nt1-nt6: SacI restriction site
<221> NAME/KEY: misc_feature
<223> OTHER INFORMATION: nt729-nt734, nt2811-nt2816, nt5103-nt5108:
    BglII restriction site nt3335-nt3340: HindIII site

<400> SEQUENCE: 4

```
gagctcatgt gaccgttctc ggtgagttca gagataacgt ttagacttcc cttatcagcc      60
tcgtgcgggc acctataggg tttgtctgag tcaatctccg atgtcagcca agaaagaaca     120
gagcatacga gtaaatctcc cgtcttgctg taatcaagaa tttggattga agtcaagaaa     180
ttttatctcg gcaggtacac catctcttca ttccgtattc cttgtcgaga tccaccaacc     240
gttctcgagt gatcgagaag gtgtagaatc tgcgacggag cttgtcgac atttgtcgta     300 ctcgccttag tcgatcttgg tgtagaacca tagagacatg gagccttcgt caatgtcgaa     360
tagaattttc ctgaaatcaa tactcataaa agaatattag atagaaataa cccccgagcg     420
aacgctcaaa gggtaacatg ttatacaatg tatggaaaac tgaaaatgaa ttaaatttac     480
agaccaatgt tttgtatatg agcgtctact cttttaccga cttcgatcag tcaatttgtt     540
aagttatata ctttccctag cccctagcct tgtcgttgga gaatcgttct cggaagataa     600
ggctcttgga ccttttgacct gcctcggttg aacaagcact aatcctagcc cccagccgtg    660
aagttggaaa acccgatttc cgattacacg gcttggttaa tacgcacggc gagaactctt    720
acacgaccag atcttacatg gtcttttgtc tctacagtat ccgacaaggc cttattggct    780
ctgggcgtcc ccagccgaag ttcccttagg ttcctcggag gccttgtcaa gacggtgtaa    840 aggacagta ggataggttt caacgctagg tgtcatcgtg gtaagggatc tctgggtaaa     900
acacttggcg atcttgtgta cctgatatca actttgttgg agtaaaggta atgggagaat    960
cgctacacct ctggttgagg accaggtggt agtcgcaact cgaccacttg aagtagaaat   1020
agtgggagaa tcgctacacc gctggtcgag aaccaagtag tagtctaaac tcgaccacta   1080
gaattaaagg tagtgggaga atcgctacac cgctggtcga gaactaggta tagtctaaac   1140
tcgaccacta gaagtaaagg tagtgggaga atcgctacac cgctggtcga ggaccaggta   1200
```

```
gtagtcgtaa ctcgaccact agaagtggaa atagtgggag aatcgctaca ccgctggtcg    1260
agaaccaggt gtaatctaaa ctcgaccact tgaagtaaat gtgcgagaga tcgctacgat    1320
tgacgggtct agaaccagtg agtaggtgtc tctcaaccat cttaagtcat ggtgcgagga    1380
ctgctgcgtt attgctgtag tcgtacctcg accatctaaa gttaaggtgc gagagattgc    1440
tacgttttac tagttcaaga accagcgagc gagtagaatt atctctcgaa caccaatgaa    1500
agttgcggtg cgagagattg ctacgtactg gttcgaggac catcgagcga gtagaattat    1560
ctctcgaaca ccaatggaag ttgcggtgcg agagatttct acgtactggt tcgagaacca    1620
gcgagcgagt agaatcatct ctcgaacacc aatggaggtt gcggtgcgaa agattaatat    1680
gcactggttc gaggaccagc gaacgtgtag agttatatct cgaacaccaa tggaagttgc    1740
ggtgcgagag attgctacgt actagttcga ggaccatcga gcgagtagaa ttatttctcg    1800
aacaccaatg gaagttgcgg tgcgagagat tgctacgtac tggttcgaga accagcgagc    1860
gagtagaatt atctctcgaa caccaatgga agtttgcggt gcgagagatt gctacgtact    1920
ggttcaagaa ccatggaagt tgcggtgcga gagatttcta tgtactggtt cgaggaccag    1980
ggagcgagta gaattatctc tcgaacacca atggaagttt gcggtgcgag agattgctac    2040
gtactggttc gagaaccagt gaatgtgtag agttatctct cgaacaccaa tggaggttgc    2100
ggtgcgagag attgctacgt actggttcga gaaccagcga acgtgtagag ttatctctcg    2160
aacacatgga ggttgcggtg cgagagattg ctacgtactg gttcgaggac cagtgaacgt    2220
gtagagttat ctctcgaaca ccaatggagg tgctagagtt ggtttattac atatgcgtct    2280
catgtggcca gcatgactca cacacccaac ttgtagcata tccggatgtc tgttcgcaag    2340
catgtcgggt gatcaagccg acagcgctcg cgaggaatta tccgttaaca accttttctc    2400
gagtagtcta gccatggcgg gtgctatgag ataggtcgtc ggtcttcgtt ggtgggttgg    2460
gcgtgacgac tttgcatttg tcgagatcgt tctcgataat gcggtgtact tgaccacaac    2520
ctagtcgagt gctcaattgt tcctgaaaaa tattttctag aagacaagac atatagcaga    2580
taatatcgag tatgtactca gaaaactgca tggatcttct agtattatca ggatgtaacg    2640
agcagatgta aatattaggc attatgtaaa ccgtaaacaa gcatgattca tacaaaagag    2700
aatagagcga gccccagtgt tagaccgttg tcggcctaac accggaaaca ctcacataat    2760
aaatattgta taaaaaacat gctctaggta aacataataa attatattat agatctgaca    2820
attctgtatg atctgaatag gtacgataaa ttgcatataa aatattgcgt accttgtag    2880 atacatgccg gatgtatcta cgaaattagt agattcaatc tactgaatac ctttgccttc    2940
ttggtgagga acagcaactc cttaatatgc ttttgcgtgc atggtactgt cccccgtgca    3000
cgtaccatgt aatctggtca tttaattgac ctgtttgtct ttagccccga gtcagattgc    3060
tgcctagaga ttggatagta gtgcagacgt ggaaactccc cgagtccgac tagcatttac    3120
accaataagc agatcaatcc gacgctttga tttccgctcc acgacgcgct tgttttgttg    3180
gtggagatcg atgccgtgtt cggcttggac gcggttaatc gagccctcca ccagttgatg    3240
tggcgcgtgt attggtactg atcaatctcg aaggttgtct gcactgttga ttgacaacct    3300
caaaattgac gtgatccacg gcattgacgt cttgaagctt gagcgatcct gataaatcga    3360
atttgttgac gacgattgtt ccgatctcgt cgggacacgt attctggtag gtttagatca    3420
cccaacagcg aagttgtcga gtagattgtt gtcggagaat ccatctctta aacccatctc    3480
gtcgaaatcc tgaagcacca aaatccccct acctggcgtg ccattatcga cgtttgatgt    3540
ctcgactacg gtatttgcat gtcatggggg atcgttggta ctaggatata cgcgagactg    3600
```

```
acgtaaaaga gatggagaca gggattttta tacaggttcg ggcccctgaa ttgtcatata    3660
ataaccctac atcctgttgg ccgaagccgg tattgctctt attcatgata atcacaccat    3720
tacaatattt agggtagcct atctaactat tgtcgacatg gcggtctgac gatctgactc    3780
gtagtcgaca acagggtagc cttcctcctc gaacctgtgc ctgacgagat cagagatagc    3840
gctttcgtct ctcctgacag tatcctgaga caccgtaggg gacttgtcgt gcctatctct    3900
gaagtcgata tccggcgtct tgtcttggcg tatgttggct tgtattggct tgtggctttg    3960
tggcgtttat gttgctcgta tattgtggtg ggtgtgtatt gtccgtgtct tgtatggtgg    4020
gtgtcgattg tgtcccattt ccttctaggg gaccttgtat ttatacccat aggtgtcccc    4080
ttgtccaagt agaactaggg aaaccaatat ggatacaatc cgattagtcc tttgtcgttt    4140
ccatgtagaa ctttggttgt ctttctttat ccggaactcc tcctatatcc gcaggttatt    4200
ttcgtatagg acatgttatg tggtgggtcc taccgagatt tagtcaacta ctattaggta    4260
tgtggtatcc ataaccctga cataccat gatttttctg tctatcaata actgcctcgg    4320
tgaacttgaa gaagtaggtt gttattgcag caataatgag acaaactagt atttatttat    4380
gatatccctt ggttaagtag tcatgcgtta taataggaac ctctaattcc ctcgtaaata    4440
cagctaagtt tattataaca agagctttaa taatattaaa attgtagcct tttttggatt    4500
tgtacgaaat aattagcctt aaaaaacatt taatgttggt tagctcaaaa tatttggaaa    4560
tggagtgagt atatgttact gacttcaaaa atttttcaaa cggtattcat gtcgttttcg    4620
tgagtggact gaaacagcag taattacatt gaacatttga acacctgtat aaagtattaa    4680
atatatacta aaaaataatt aattatacat attacgacta atttgcaaga cgaatctttt    4740
aagcataatt gctccatgat ttaacaatat agtgctacag taaacatgtg ctaatgacgg    4800
attaattagg cttaataaat tcgtctcacg tttactgacg gattctataa ttgatttttt    4860
tattaatgcc caaacacccc atacaacact ctatataata ctcaatgtga cgtgccaaaa    4920
ctttagacac ctggatgtaa acaccactct gttccttctc ctctataaat ggcaccgggg    4980
tggtttgtcg gcaccaaagg cagaaaagaa agcca atg gcg tct tca ggc ctc       5033
                                        Met Ala Ser Ser Gly Leu
                                         1               5 gca gtt gca gca aca gcc tcg tca gcc tgg ctc tgc tgc ccc aat cat       5081
Ala Val Ala Ala Thr Ala Ser Ser Ala Trp Leu Cys Cys Pro Asn His
        10                  15                  20 cac atc cat acc agc agc agc aga tct cgc aag cat ctt ctt ctc cat       5129
His Ile His Thr Ser Ser Ser Arg Ser Arg Lys His Leu Leu Leu His
    25                  30                  35 ggc ctg tac ggg tct gca cct gca cgt act agg tatagtagct gcaactttat     5182
Gly Leu Tyr Gly Ser Ala Pro Ala Arg Thr Arg
    40                  45 tcacaatgtg atgtcacgtt attatatatg tttcgtcgtc aatggcggcg aaccttgcag     5242 g gga cga cgg ccg ccg gtg tgg act gcg gcg gcg gcc acc gca gca gcg     5291
  Gly Arg Arg Pro Pro Val Trp Thr Ala Ala Ala Ala Thr Ala Ala Ala
  50                  55                  60                  65 ccg gcg gac acg gcg gcg tcg gcg cgg cgg gag cag gtg gag atc gcc       5339
Pro Ala Asp Thr Ala Ala Ser Ala Arg Arg Glu Gln Val Glu Ile Ala
            70                  75                  80 cgg tcg ctg aac gcg tgg gtg gag gag aac atg ctc ccg ctg ctc acc       5387
Arg Ser Leu Asn Ala Trp Val Glu Glu Asn Met Leu Pro Leu Leu Thr
        85                  90                  95 ccc gtc gac                                                           5396
Pro Val Asp
```

<210> SEQ ID NO 5
<211> LENGTH: 325
<212> TYPE: DNA
<213> ORGANISM: Oryza sativa L.
<220> FEATURE:
<221> NAME/KEY: misc_feature
<223> OTHER INFORMATION: Variety: IR24
    Library name: lambdaDASHII genomic library derived from green leaf
    genomic DNA Clone name: RPG106 SacI-SalI 5.4 kb
<221> NAME/KEY: misc_feature
<223> OTHER INFORMATION: Strandedness: double - Topology: linear
    Molecular Type: modified genomic DNA
    Feature nt1-nt3: the latter half of StuI restriction site
    nt321-nt325: the first half of blunt-ended MluI restriction site
<221> NAME/KEY: misc_feature
<223> OTHER INFORMATION: nt100: introduction of mutation (T to A)
    nt133-nt213: the first intron of RPC213 gene

<400> SEQUENCE: 5
cctcgcagtt gcagcaacag cctcgtcagc ctggctctgc tgccccaatc atcacatcca      60
taccagcagc agcagatctc gcaagcatct tcttctccaa ggcctgtacg ggtctgcacc     120
tgcacgtact aggtatagta gctgcaactt tattcacaat gtgatgtcac gttattatat     180
atgtttcgtc gtcaatggcg gcgaaccttg caggggacga cggccgccgg tgtggactgc     240
ggcggcggcc accgcagcag cgccggcgga cacggcggcg tcggcgcggc gggagcaggt     300
ggagatcgcc cggtcgctga acgcg                                          325

<210> SEQ ID NO 6
<211> LENGTH: 244
<212> TYPE: DNA
<213> ORGANISM: Oryza sativa L.
<220> FEATURE:
<221> NAME/KEY: misc_feature
<223> OTHER INFORMATION: Variety: IR24 - Tissue: pistil
    Library name: lambdaZAPII cDNA library derived from pistil mRNA
    Clone name: RPC213
<221> NAME/KEY: misc_feature
<223> OTHER INFORMATION: Strandedness: double - Topology: linear
    Molecular type: modified cDNA to mRNA
<221> NAME/KEY: misc_feature
<223> OTHER INFORMATION: nt1-nt3: the latter half of restriction site
    StuI nt240-nt244: the first half of blunt-ended restriction site
    MluI nt100: introduction of mutation (T to A)

<400> SEQUENCE: 6
cctcgcagtt gcagcaacag cctcgtcagc ctggctctgc tgccccaatc atcacatcca      60
taccagcagc agcagatctc gcaagcatct tcttctccaa ggcctgtacg ggtctgcacc     120
tgcacgtact aggggacgac ggccgccggt gtggactgcg gcggcggcca ccgcagcagc     180
gccggcggac acggcggcgt cggcgcggcg ggagcaggtg gagatcgccc ggtcgctgaa     240
cgcg                                                                 244

<210> SEQ ID NO 7
<211> LENGTH: 374
<212> TYPE: DNA
<213> ORGANISM: Oryza sativa L.
<220> FEATURE:
<221> NAME/KEY: misc_feature
<223> OTHER INFORMATION: Variety: IR24
    Library name: green leaf genomic DNA -R- lambdaDASHII genomic
    library Clone name: RPG106 SacI-SalI 5.4 kb
<221> NAME/KEY: misc_feature
<223> OTHER INFORMATION: Strandedness: double - Topology: linear
    Molecular type: modified genomic DNA
    Feature: nt1, nt2: transcription initiation points of RPC213 gene

```
        determined by primer extension
<221> NAME/KEY: misc_feature
<223> OTHER INFORMATION: nt22: introduction of mutation (T to A)
      nt134: introduction of mutation (T to A)
      nt167-nt247: the first intron of RPC213 gene

<400> SEQUENCE: 7
aaaggcagaa aagaaagcca aaggcgtctt caggcctcgc agttgcagca acagcctcgt      60
cagcctggct ctgctgcccc aatcatcaca tccataccag cagcagcaga tctcgcaagc     120
atcttcttct ccaaggcctg tacgggtctg cacctgcacg tactaggtat agtagctgca     180
actttattca caatgtgatg tcacgttatt atatatgttt cgtcgtcaat ggcggcgaac     240
cttgcagggg acgacggccg ccggtgtgga ctgcggcggc ggccaccgca gcagcgccgg     300
cggacacggc ggcgtcggcg cggcgggagc aggtggagat cgcccggtcg ctgaacgcgt     360
gggtggagga gaac                                                       374

<210> SEQ ID NO 8
<211> LENGTH: 293
<212> TYPE: DNA
<213> ORGANISM: Oryza sativa L.
<220> FEATURE:
<221> NAME/KEY: misc_feature
<223> OTHER INFORMATION: Variety: IR24 - Tissue: Pistil
      Library name: lambdaZAPII cDNA library derived from pistil mRNA
      Clone name: RPC213
<221> NAME/KEY: misc_feature
<223> OTHER INFORMATION: Strandedness: double - Topology: linear
      Molecular type: modified cDNA to mRNA
      Feature: nt1, nt2: transcription intitiation points of RPC213 gene
      determined by primer extension
<221> NAME/KEY: misc_feature
<223> OTHER INFORMATION: nt22: introduction of mutation (T to A)
      nt134: introduction of mutation (T to A)

<400> SEQUENCE: 8
aaaggcagaa aagaaagcca aaggcgtctt caggcctcgc agttgcagca acagcctcgt      60
cagcctggct ctgctgcccc aatcatcaca tccataccag cagcagcaga tctcgcaagc     120
atcttcttct ccaaggcctg tacgggtctg cacctgcacg tactagggga cgacggccgc     180
cggtgtggac tgcggcggcg gccaccgcag cagcgccggc ggacacggcg gcgtcggcgc     240
ggcgggagca ggtggagatc gcccggtcgc tgaacgcgtg ggtggaggag aac            293

<210> SEQ ID NO 9
<211> LENGTH: 20
<212> TYPE: DNA
<213> ORGANISM: Artificial Sequence
<220> FEATURE:
<223> OTHER INFORMATION: 213S primer

<400> SEQUENCE: 9
cgctatggcc cgtttcagct                                                  20

<210> SEQ ID NO 10
<211> LENGTH: 21
<212> TYPE: DNA
<213> ORGANISM: Artificial Sequence
<220> FEATURE:
<223> OTHER INFORMATION: 213AS primer

<400> SEQUENCE: 10
gtcgtcctgt cgcttcatta c                                                21

<210> SEQ ID NO 11
```

```
<211> LENGTH: 24
<212> TYPE: DNA
<213> ORGANISM: Artificial Sequence
<220> FEATURE:
<223> OTHER INFORMATION: Primer synthesized on the basis of rice actin 1
      gene sequence

<400> SEQUENCE: 11
gtatccatga gactacatac aact                                           24

<210> SEQ ID NO 12
<211> LENGTH: 22
<212> TYPE: DNA
<213> ORGANISM: Artificial Sequence
<220> FEATURE:
<223> OTHER INFORMATION: Primer synthesized on the basis of rice actin 1
      gene sequence

<400> SEQUENCE: 12
tactcagcct tggcaatcca ca                                             22

<210> SEQ ID NO 13
<211> LENGTH: 19
<212> TYPE: DNA
<213> ORGANISM: Artificial Sequence
<220> FEATURE:
<223> OTHER INFORMATION: 213Z Primer

<400> SEQUENCE: 13
tgctggtatg gatgtgatg                                                 19

<210> SEQ ID NO 14
<211> LENGTH: 18
<212> TYPE: DNA
<213> ORGANISM: Artificial Sequence
<220> FEATURE:
<223> OTHER INFORMATION: 213Z-2 Primer

<400> SEQUENCE: 14
ctgacgaggc tgttgctg                                                  18

<210> SEQ ID NO 15
<211> LENGTH: 22
<212> TYPE: DNA
<213> ORGANISM: Artificial Sequence
<220> FEATURE:
<223> OTHER INFORMATION: 213P-5H-2 Primer

<400> SEQUENCE: 15
gacgtgatcc acggcattga cg                                             22

<210> SEQ ID NO 16
<211> LENGTH: 27
<212> TYPE: DNA
<213> ORGANISM: Artificial Sequence
<220> FEATURE:
<223> OTHER INFORMATION: 213P 2ndATG-Bam Primer

<400> SEQUENCE: 16
cggggatccg ttctcctcca cccacgc                                        27

<210> SEQ ID NO 17
<211> LENGTH: 33
<212> TYPE: DNA
<213> ORGANISM: Artificial Sequence
<220> FEATURE:
<223> OTHER INFORMATION: 213inFw1 Primer
```

```
<400> SEQUENCE: 17
gggtctagac ctgcacgtac taggtatagt agc                          33

<210> SEQ ID NO 18
<211> LENGTH: 27
<212> TYPE: DNA
<213> ORGANISM: Artificial Sequence
<220> FEATURE:
<223> OTHER INFORMATION: 213inRV1 Primer

<400> SEQUENCE: 18
caccccgggc cgtcgtcccc tgcaagg                                 27

<210> SEQ ID NO 19
<211> LENGTH: 31
<212> TYPE: DNA
<213> ORGANISM: Artificial Sequence
<220> FEATURE:
<223> OTHER INFORMATION: 2131edFW1 Primer

<400> SEQUENCE: 19
tcgtctagaa aggcagaaaa gaaagccaat g                            31

<210> SEQ ID NO 20
<211> LENGTH: 29
<212> TYPE: DNA
<213> ORGANISM: Artificial Sequence
<220> FEATURE:
<223> OTHER INFORMATION: 2131edRV1 Primer

<400> SEQUENCE: 20
agcgggcccg ggttctcctc cacccacgc                               29

<210> SEQ ID NO 21
<211> LENGTH: 36
<212> TYPE: DNA
<213> ORGANISM: Artificial Sequence
<220> FEATURE:
<223> OTHER INFORMATION: 2131edFW-atg Primer

<400> SEQUENCE: 21
tcgtctagaa aggcagaaaa gaaagccaaa ggcgtc                       36

<210> SEQ ID NO 22
<211> LENGTH: 20
<212> TYPE: DNA
<213> ORGANISM: Artificial Sequence
<220> FEATURE:
<223> OTHER INFORMATION: 213FWlink Primer

<400> SEQUENCE: 22
cttctccaag gcctgtacgg                                         20

<210> SEQ ID NO 23
<211> LENGTH: 20
<212> TYPE: DNA
<213> ORGANISM: Artificial Sequence
<220> FEATURE:
<223> OTHER INFORMATION: 213RVlink Primer

<400> SEQUENCE: 23
ccgtacaggc cttggagaag                                         20

<210> SEQ ID NO 24
```

-continued

```
<211> LENGTH: 20
<212> TYPE: DNA
<213> ORGANISM: Artificial Sequence
<220> FEATURE:
<223> OTHER INFORMATION: 213FW5Bg Primer

<400> SEQUENCE: 24
ccaatcatca catccatacc                                              20

<210> SEQ ID NO 25
<211> LENGTH: 17
<212> TYPE: DNA
<213> ORGANISM: Artificial Sequence
<220> FEATURE:
<223> OTHER INFORMATION: 213RV3E52 Primer

<400> SEQUENCE: 25
ccgccgcagt ccacacc                                                 17
```